(12) United States Patent
Berge

(10) Patent No.: US 7,659,242 B2
(45) Date of Patent: Feb. 9, 2010

(54) COMPOSITION COMPRISING PROTEIN MATERIAL AND COMPOUNDS COMPRISING NON-OXIDIZABLE FATTY ACID ENTITIES

(75) Inventor: Rolf Berge, Bønes (NO)

(73) Assignee: Thia Medica AS, Bergen (NO)

( * ) Notice: Subject to any disclaimer, the term of this patent is extended or adjusted under 35 U.S.C. 154(b) by 627 days.

(21) Appl. No.: 10/550,033

(22) PCT Filed: Jul. 19, 2005

(86) PCT No.: PCT/NO2005/000272

§ 371 (c)(1),
(2), (4) Date: May 9, 2006

(87) PCT Pub. No.: WO2006/009465

PCT Pub. Date: Jan. 26, 2006

(65) Prior Publication Data

US 2007/0015795 A1    Jan. 18, 2007

(30) Foreign Application Priority Data

Jul. 19, 2004  (NO) .................. 20043091
Jul. 19, 2004  (NO) .................. 20043093
Dec. 17, 2004  (NO) .................. 20045544

(51) Int. Cl.
*A61K 38/00*  (2006.01)
*A61K 38/28*  (2006.01)
*A61K 38/16*  (2006.01)
*A61K 31/20*  (2006.01)

(52) U.S. Cl. .............. 514/2; 514/3; 514/4; 514/5; 514/6; 514/7; 514/8; 514/9; 514/10; 514/11; 514/12; 514/560; 514/561

(58) Field of Classification Search .............. 514/2–12, 514/560, 561
See application file for complete search history.

(56) References Cited

U.S. PATENT DOCUMENTS

| | | |
|---|---|---|
| 6,365,628 B1 | 4/2002 | Berge |
| 6,417,232 B1 | 7/2002 | Berge |
| 6,441,036 B1 | 8/2002 | Berge |
| 2002/0198259 A1 | 12/2002 | Berge |

FOREIGN PATENT DOCUMENTS

| | | |
|---|---|---|
| EP | 0 843 972 | 5/1998 |
| WO | WO 99/58121 | 11/1999 |
| WO | WO 99/58122 | 11/1999 |
| WO | WO 02/063976 | 8/2002 |
| WO | WO 02/064809 | 8/2002 |
| WO | WO 2004/000854 | 12/2003 |
| WO | WO2005/002605 | 1/2005 |
| WO | WO2005/002606 | 1/2005 |

OTHER PUBLICATIONS

Moya-Falcon, C., et al. (2004) Effects of 3-thia fatty acids on feed intake, growth, tissue fatty acid composition, -oxidation and Na$^+$, K$^+$-ATPase activity in Atlantic salmon. Comparative Biochemistry and Physiology, Part B. 139B:657-668.

*Primary Examiner*—Raymond J Henley, III
(74) *Attorney, Agent, or Firm*—Ladas & Parry LLP

(57) ABSTRACT

The present invention concerns a composition prepared from a combination of non β-oxidizable fatty acid entities and a protein material, and the use of said composition for the preparation of a pharmaceutical or nutritional composition for the prevention and/or treatment of insulin resistance, obesity, diabetes, fatty liver, hypercholesterolemia, dyslipidemia, atherosclerosis, coronary heart disease, thrombosis, stenosis, secondary stenosis, myocardial infarction, stroke, elevated blood pressure, endothelial dysfunction, procoagulant state, polycystic ovary syndrome, the metabolic syndrome, cancer, inflammatory disorders and proliferate skin disorders. An alternative embodiment of the invention includes oil in the composition The present invention also concerns an animal feed prepared from a combination of a protein material and a compound comprising non β-oxidizable fatty acid analogues, the use of said feed for improving the body composition of an animal, and a product produced from said animal.

155 Claims, 4 Drawing Sheets

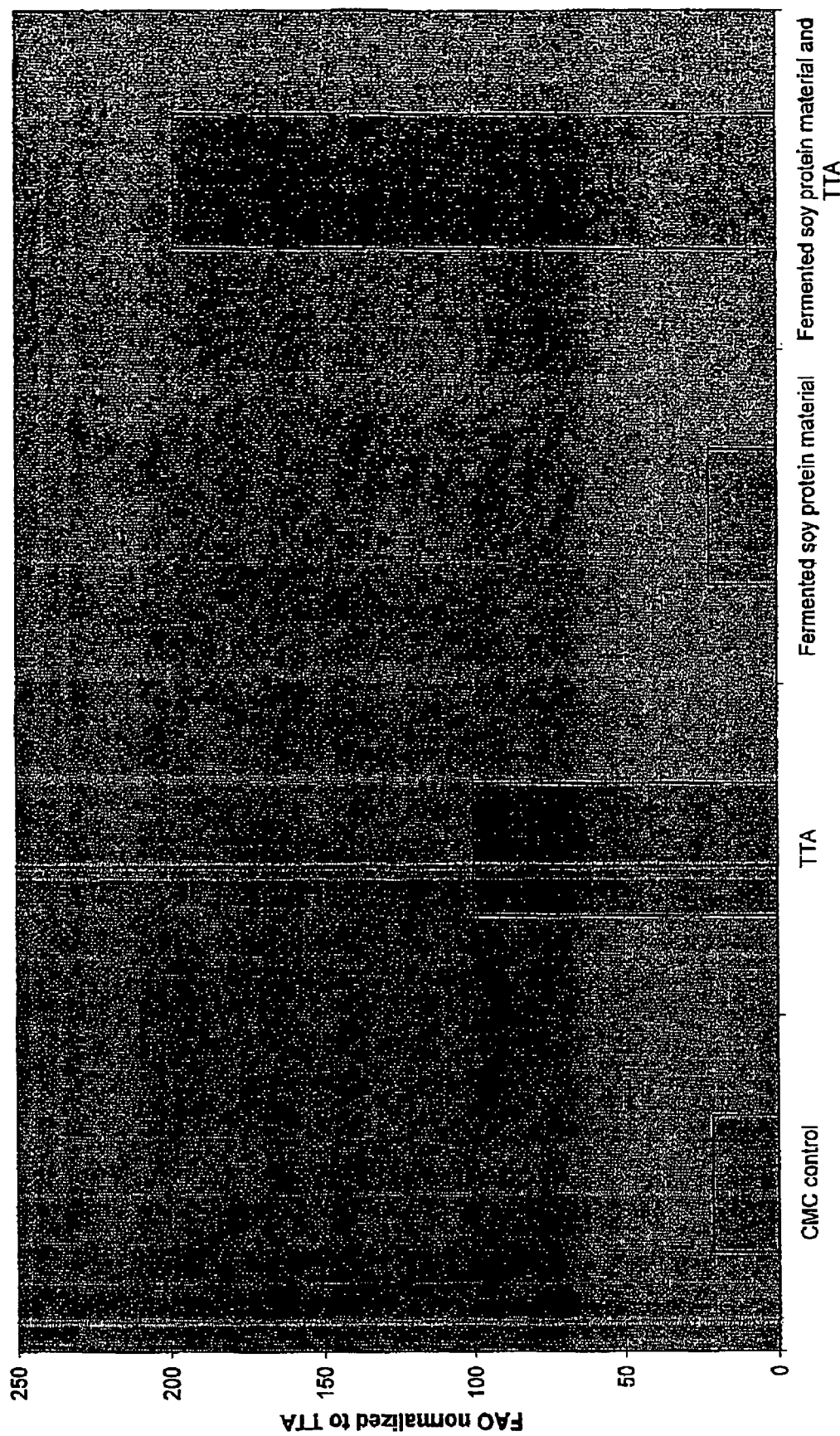

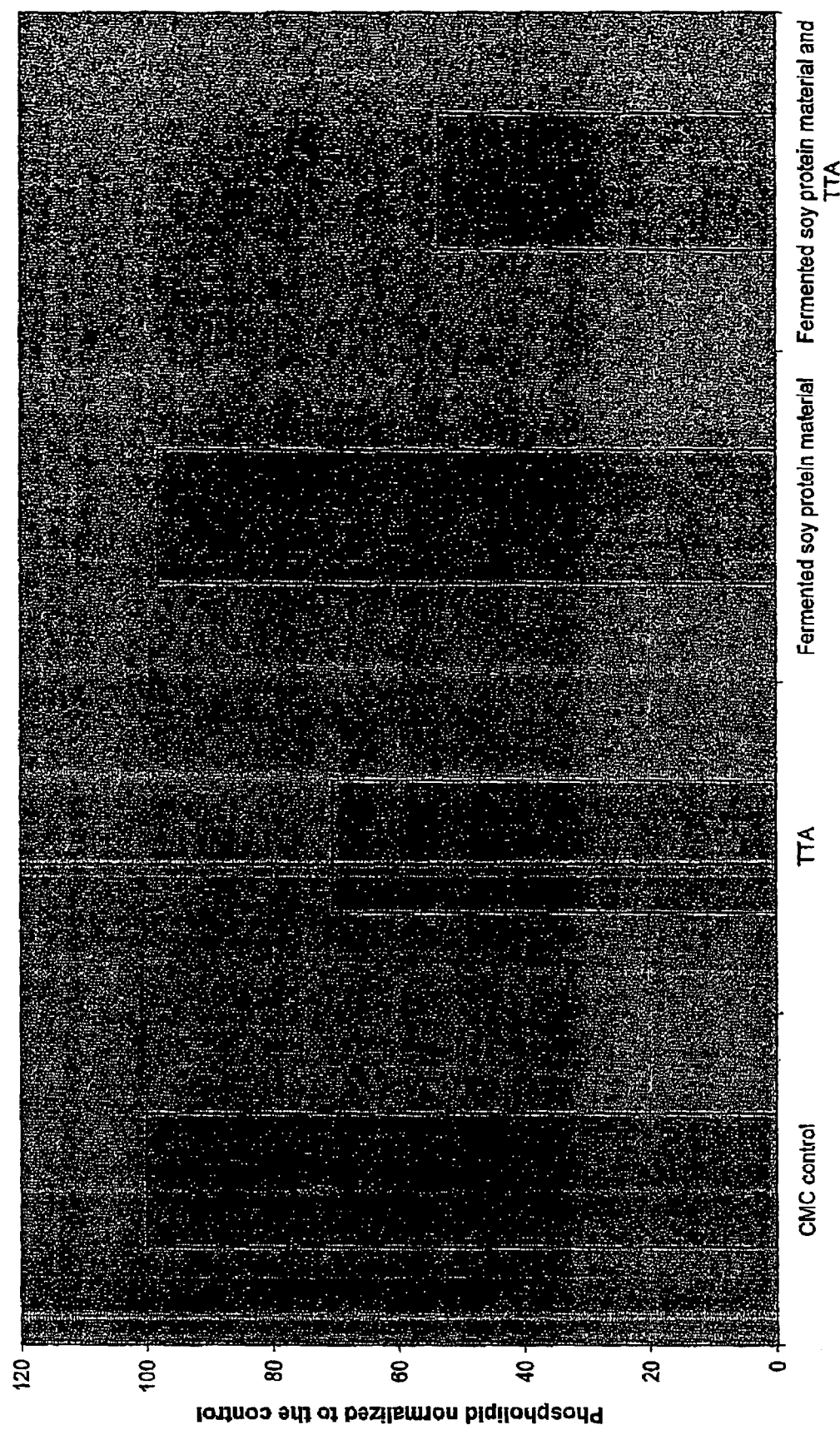

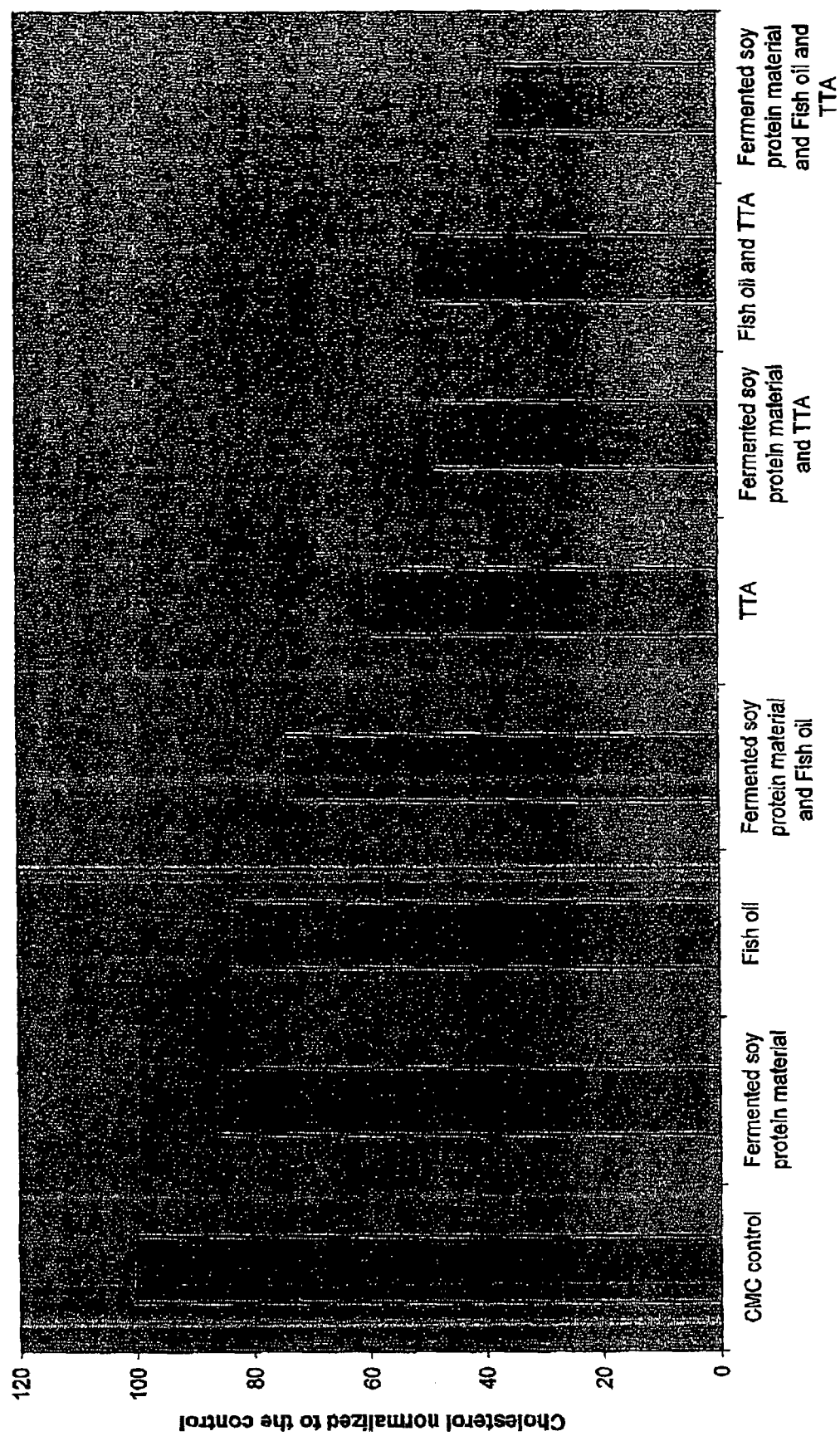
Fig. 3: Plasma Cholesterol levels.

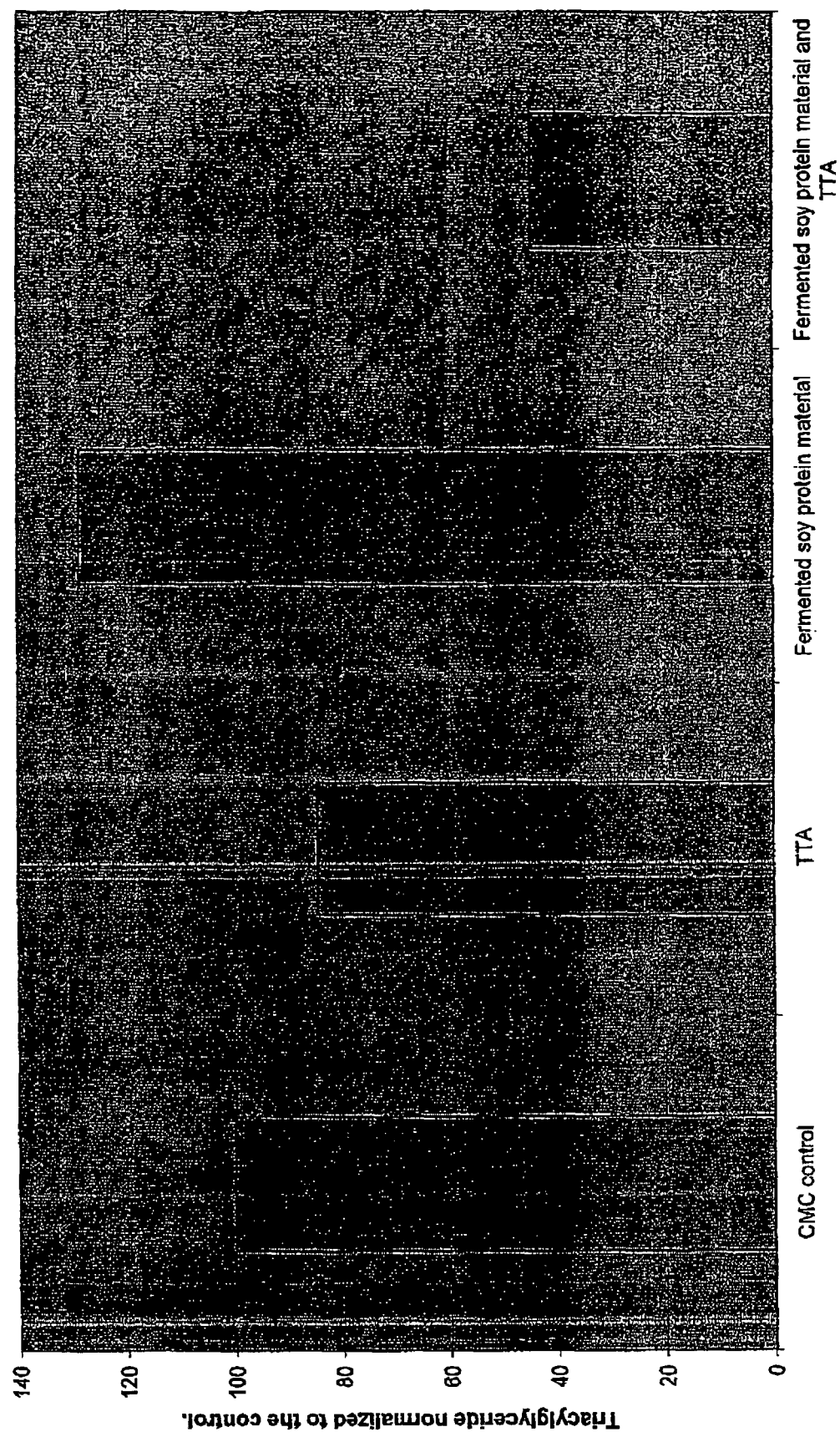
Fig. 4: Plasma Triacylglyceride levels.

COMPOSITION COMPRISING PROTEIN MATERIAL AND COMPOUNDS COMPRISING NON-OXIDIZABLE FATTY ACID ENTITIES

FIELD OF INVENTION

The use of a combination of non β-oxidizable fatty acid entities and a protein material has shown surprising synergistic effects. The present invention concerns a composition prepared from a combination of compounds comprising non β-oxidizable fatty acid entities and a protein material, and the use of said composition for the preparation of a pharmaceutical or nutritional composition for the prevention and/or treatment of insulin resistance, obesity, diabetes, fatty liver, hypercholesterolemia, dyslipidemia, atherosclerosis; coronary heart disease, thrombosis, stenosis, secondary stenosis, myocardial infarction, stoke, elevated blood pressure, endothelial dysfunction, procoagulant state, polycystic ovary syndrome, the metabolic syndrome, cancer, inflammatory disorders and proliferate skin disorders. Said composition may also be used as an additive to animal fodder for routine feeding of animals in order to affect their body composition in general and fatty acid composition specifically.

BACKGROUND OF THE INVENTION

In earlier patent applications, the inventor has described beneficial applications of the non β-oxidizable fatty acid analogues of the present invention in the treatment and prevention of obesity (NO 2000 5461), diabetes (NO 2000 5462), primary and secondary stenosis (NO 2000 5463), cancer (NO 2002 5930), proliferate skin disorders (NO 2003 1080), inflammatory and autoimmune disorders (NO 2003 2054). In other earlier patent applications, the inventor has described beneficial applications of protein materials of the present invention, including a sine cell protein material (NO 2003 3082), and a fish protein hydrolysate (NO 2003 3078).

Surprisingly, the present inventors have shown that the use of a combination of non β-oxidizable fatty acid entities with a protein material has synergistic beneficial biological effects, The inventors show that the combination of non β-oxidizable fatty acid entities with a protein material lowers the concentration of plasma cholesterol, triglycerides and phospholipids, and increase fatty acyl CoA oxidase activity. In addition, the inventors describe how non β-oxidizable fatty acid entities and a protein material can be directly added to animal feed The feed is digestible, and has shown surprising effects on the fatty acid composition of the animals. Based on these unexpected findings, it is anticipated that the combination of non β-oxidizable fatty acid entities and a protein material will have an increased preventive and/or therapeutic effect on all the diseases the non β-oxidizable fatty acid entities are effective against, compared to that of the fatty acid entities alone.

DETAILED DESCRIPTION OF THE INVENTION

The present invention relates to the use of a preparation comprising a combination of:
1) a protein material, and
2) one or more compounds comprising non β-oxidizable fatty acid entities represented by
(a) the general formula R"—COO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group; and R" is a hydrogen atom or an alkyl group containing from 1 to 4 carbon atoms; and/or
(b) the general formula (I),

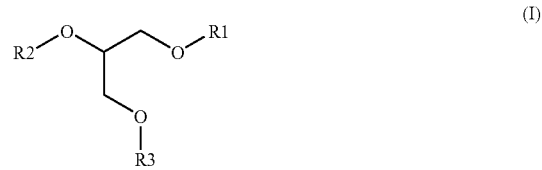

wherein R1, R2, and R3 represent
i) a hydrogen atom; or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or
(c) the general formula (II),

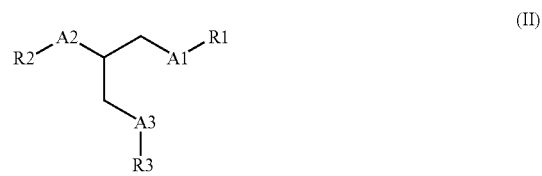

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;
wherein R1, R2, and R3 represent
i) a hydrogen atom or a linear or branched alkyl group, saturated or unsaturated, optionally substituted, containing from 1 to 23 carbon atoms; or
ii) a group having the formula CO—R in which R is a linear or branched alkyl group, saturated or unsaturated, optionally substituted, and the main chain of said R contains from 1 to 25 carbon atoms; or iii) a group having the formula CO—(CH$_2$)$_{2n+1}$—X—R', wherein X is a sulphur atom, a selenium atom, an oxygen atom, a CH$_2$ group, a SO group or a SO$_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a CH$_2$ group, a SO group and a SO$_2$ group;

iv) an entity selected from the group composing —PO$_3$CH$_2$CHNH$_3$COOH (serine), PO$_3$CH$_2$CH$_2$NH$_3$ (ethanolamine), PO$_3$CH$_2$CH$_2$N(CH$_3$)$_3$ (choline), PO$_3$CH$_2$CHOHCH$_2$OH (glycerol) and PO$_3$(CHOH)$_6$ (inositol);

wherein R1, R2, and R3 are chosen independently from i), ii), iii), or iv), but at least one of R1, R2, or R3 is defined by iii); and/or a salt, prodrug or complex of the compounds according to (a)-(c).

In a preferred embodiment of a compound according to the invention at least one of R1, R2 or R3 is an alkyl.

In a preferred embodiment of a compound according to the invention at least one of R1, R2 or R3 is an alkene.

In a preferred embodiment of a compound according to the invention at least one of R1, R2 or R3 is an alkyne.

In a preferred embodiment of a compound according to the invention at least one of R1, R2 or R3 is tetradecylthioacetic acid.

In a preferred embodiment of a compound according to the invention at least one of R1, R2 or R3 is tetradecylselenoacetic acid.

Preferred embodiments of the compounds according to the invention are non β-oxidizable fatty acids.

In a preferred embodiment of a compound according to the invention X is a sulphur atom or a selenium atom.

Preferred embodiments of the compounds according to the invention are tetradecylthioacetic acid (TTA), tetradecylselenoacetic acid and 3-Thia-15-heptadecyne.

In a preferred embodiment of a compound according to the invention n is 0 or 1.

In a preferred embodiment of a compound according to the invention said compound is a phospholipid, wherein said phospholipid is selected from the group comprising phosphatidyl serine, phosphatidyl choline, phosphatidyl ethanolamine, phosphatidyl inositol, phosphatidyl glycerol, diphosphatidyl glycerol.

In a preferred embodiment of a compound according to the invention said compound is a triacylglycerol.

In a preferred embodiment of a compound according to the invention said compound is a diacylglycerol.

In a preferred embodiment of a compound according to the invention said compound is a monoacylglycerol.

In a preferred embodiment of a compound according to the invention said compound is the phosphatidylcholine (PC) derivative 1,2-ditetradecylthioacetoyl-sn-glycero-3-phosphocholine.

In a preferred embodiment of a compound according to the invention said compound is the phosphatidylethanolamine (PE) derivative 1,2-ditetradecylthioacetoyl-sn-glycero-3-phosphoethanolamine.

Preferred embodiments of the compounds according to the invention are mono-, di- or tri-acylglycerides.

Preferred embodiments of the compounds according to the invention are tri-acylglycerides comprising tetradecylthioacetic acid (TTA).

In a preferred embodiment of a compound according to formula (II) A1 and A3 both represent an oxygen atom, while A2 represent a sulphur atom or an N—R4 group in which R4 is a hydrogen atom or a linear or branched alkyl group, saturated or unsaturated, optionally substituted, containing from 1 to 5 carbon atoms.

The compounds according to the invention are analogues of naturally occurring compounds, and as such are recognized by the same systems which process the natural compounds, including the enzymes that β- and in some cases ω-oxidize natural long chain fatty acids. The analogues differ from their nasally occurring counterparts in that they cannot be completely oxidized in this manner.

The compounds according to the invention may be non β-oxidizable fatty acid analogues, as represented by the formula R"CCO—(CH$_2$)$_{2n+1}$—X—R'. However, said compounds may also be more complex structures derived from one or more of said non β-oxidizable fatty acid analogues, as represented by the general formulas (I) or (II). These compounds are analogues of naturally occurring mono-, di-, and triacylglycerols, or phospholipids including phosphatidyl serine, phosphatidyl choline, phosphatidyl ethanolamine, phosphatidyl inositol, phosphatidyl glycerol, and diphosphatidyl glycerol. Said compounds may also comprise a substitution in the glycerol backbone, as shown in formula (II). Said substitution of the oxygen(s) is achieved by replacing the oxygen(s) with sulphur or a nitrogen containing group. This may block hydrolysis before uptake by the intestines, thus increasing the bioavailability of the compounds.

The above complex structures derived from one or more of said non β-oxidizable fatty acid entities have their effect because the fatty acid analogues they comprise are not capable of being fully β-oxidized. Said complex structures may have an effect as complete structures, and as naturally resulting degradation products comprising the fatty acid analogues. Because the compounds are not able to be fully β-oxidized, they will build up, and this triggers an increase in the β-oxidation of naturally occurring fatty acids. Many of the effects of the compounds according to the invention are due to this increase in β-oxidation.

During β-oxidation, a fatty acid is enzymatically oxidized cleaved between carbons 2 and 3 (when counting from the carboxylic end of the fatty acid), resulting in the removal of the two carbon atoms on either side of the oxidation site as acetic acid. This step is then repeated on the now two carbons shorter fatty acid, and repeated again until the fatty acid is filly oxidized β-oxidation is the usual way in which the majority of fatty acids are catabolized in vivo. The β-oxidation blocking by the compounds according to the invention is achieved by the insertion of a non-oxidizable group in the X position in the formula of the present invention. Because the mechanism for β-oxidation is well known, X is defined as S, O, SO, SO$_2$, CH$_2$ or Se. Anyone skilled in the art would assume, without an inventive step, that these compounds would all block β-oxidation in the same manner.

In addition, the compounds may contain more than one block, i.e. in addition to X, R' may optionally comprise one or more heterogroups selected from the group comprising an oxygen atom, a sulphur atom, a selenium atom, an oxygen atom, a CH$_2$ group, a SO group and a SO$_2$ group. As an example, one may insert two or three sulphurs as X to induce a change in the degradation of the fatty acid and thus a modulated effect. Multiple sulphur atoms would also modulate the polarity and stability somewhat. From a pharmacological viewpoint it is generally desirable to be able to present a spectrum of compounds rather than just one single compound to avoid or counteract problems with resistance.

In addition to the identity of X, its position is also an issue. The distance of X from the carboxylic end of the fatty acid is defined by how many $CH_2$ groups are positioned between X and the carboxylic end of the fatty acid, which is defined by $(CH_2)_{2n+1}$, where n is an integer of 0 to 11. Thus there are an odd number of $CH_2$ groups, that is; the position of X relative to the carboxyl group is such tat X eventually blocks β-oxidation. The range of n is chosen to include all variations of the fatty acid analogue which has the desired biological effect Since β-oxidation in theory can work on infinitely long molecules, n could be infinite, but in practice this is not so. The fatty acids which normally undergo β-oxidation are usually 14 to 24 carbon atoms long, and this length is therefore most ideal for undergoing enzymatic β-oxidation. The ranges of n and R' are thus given so that the fatty acid entities will cover this range. (Likewise, option ii) of formulas (I) and (II) and define R to have 1 to 25 carbon groups, and option i) of formula (II) define the alkyl group to contain from 1 to 23 carbon atoms, to be analogous to naturally occurring compounds.) The total number of carbon atoms in the fatty acid backbone is preferably between 8 and 30, most preferably between 12 and 26. This size range is also desirable for the uptake and transport through cell membranes of the fatty acid entities of the present invention.

Although all fatty acid anagoges with an odd positioning of the β-oxidation blocker X away from the carboxylic end block β-oxidation, the extent of their biological effect may be variable. This is due to the difference in biological degradation time of the various compounds. The inventors have done experiments to show the effect of moving X further from the carboxylic fatty acid end. In these experiments the activity (in nmol/min/mg/protein) of mitochondrial β-oxidation in the liver of fatty acid analogues was measured with sulphur in the 3, 5 and 7 positions relative to the carboxyl end. The activities were 0.81 for sulphur in the $3^{rd}$ position, 0.61 for sulphur in the $5^{th}$ position, 0.58 for sulphur in the $7^{th}$ position, and 0.47 for palmitic acid, the non β-oxidation blocking control. This shows, as expected, that β-oxidation is indeed blocked by fatty acid analogues with varying positioning of the block, and that the effect thereof is lessened the further away from the carboxylic end the block is positioned at, because it takes the β-oxidation longer to reach the block so more of the fatty acid analogue is degraded by then. However, as the decline is great for going from the $3^{rd}$ to $5^{th}$ position, but small going from the $5^{th}$ to $7^{th}$ position, it is reasonable to assume that this decline will continue to be less as one moves out the chain and thus that it will be very far out indeed before no effect (compared to the control) is seen at all.

Thus, it is reasonable to include as compounds of the present invention, fatty acid entities and other compounds represented by the general formulas (I) and (II), (which comprise said fatty acid analogue(s),) which block β-oxidation at different distances from the carboxylic end of the analogues, as the compounds of the present invention all do indeed block β-oxidation, even if the effect thereof can be modulated. This modulation will after all differ under wearing conditions; in different tissues, with wearing dosages, and by changing the fatty acid analogue so that it is not so easily broken down, as will be described next. Thus it is reasonable to include in the formula all distances of the β-oxidation blocker from the carboxylic end of the fatty acid analogue which are biologically relevant Although fatty acid entities as described with a block in the X position cannot undergo β-oxidation, they may still undergo ω-oxidation. This is a much less common and slower biological process, which oxidizes the fatty acid not from the carboxylic end, but rather from the methyl/hydrophobic head group, here termed R'. In this pathway the carbon atom at the ω-end of the fatty acid is hydroxylated by a member of the cytochrome P450 enzyme family. This hydroxylated fatty acid is then converted into an aldehyde by an alcohol dehydrogenase, and subsequently this aldehyde is converted into a carboxyl group by an aldehyde dehydrogenase. As a consequence, the final product of the pathway is a dicarboxylic fatty acid, which can be degraded further by ω-oxidation from the ω-end.

ω-oxidation is believed to be the main pathway for degradation of the fatty acid entities as described with a block in the X position. Experiments were thus performed where R' was changed to block ω-oxidation, by introducing a triple bond at the methyl end of the fatty acid analogue. This resulted in the fatty acid analogue 3-thia-15-heptadecyn, which when tested showed the expected result: a substantially increased degradation time in vivo. This is important for the use of the fatty acid entities in pharmaceutical preparation, as it may potentiate the effects of the β-oxidizable fatty acid entities by further slowing down their breakdown.

Again, as with the blocking of β-oxidation, it is routine to find other fatty acid entities witch would block ω-oxidation in exactly the same manner, based upon knowledge of how ω-oxidation occurs. A double bond will for instance have the exact same effect as the triple bond did, and it is therefore included in the definition of the methyl/hydrophobic head group end of the molecule, here termed R', that it may be saturated or unsaturated. A branch may also block oxidation, so R' is defined as linear or branched.

In order to block ω-oxidation by the insertion of a substitute in R', said R' may be substituted in one or several positions with heterogroups selected from the group comprising an oxygen atom, a sulphur atom, a selenium atom, an oxygen atom, a $CH_2$ group, a SO group and a $SO_2$ group. R' may also be substituted with one or more compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl.

Thus the compounds according to the present invention are either fatty acids analogous to naturally occurring fatty acids, which are not capable of being β-oxidized, or naturally occurring lipids comprising said fatty acid analogues. In vivo, the fatty acid entities show a strong preference for being incorporated into phospholipids. In some cases it is indeed advantageous to mimic nature and incorporate the fatty acid entities in naturally occurring lipids, such as mono-, di-, and triglycerides and phospholipids. This changes the absorption of the compounds (when comparing fatty acids to fatty acids incorporated in larger lipid structures) and may increase the bioavailability or stability.

As an example, one could make a complex by including a fatty acid(s) which are not capable of being β-oxidized into a triacylglycerol. Such compounds are encompassed by formulas (I) and (II). If such a triacylglycerol was taken orally, for instance in an animal feed product, it would probably be transported like any triacylglycerol, from the small intestine in chylomicrons and from the liver in the blood in lipoproteins to be stored in the adipose tissue or used by muscles, heart or the liver, by hydrolyzes of the triacylglycerol into glycerol and 3 free fatty acids. The See fatty acids would at this point be the parent compound of the present invention, and not a complex anymore.

Yet other possible glycerophospholipid derivatives of the fatty acids of the present invention includes, but are not limited to, phosphatidyl cholines, phosphatidyl ethanolamines, phosphatidyl inositols, phosphatidyl serines and phosphatidyl glycerols.

Another esterification of fatty acids found in vivo which could be easily used to make a complex for a compound of the present invention would be to make the alcohol or polyalcohol corresponding to the fatty acid, for example one could make a sphingolipid derivative such as ceramide or sphingomyelin by making the corresponding amino alcohol. Like the glycerophospholipid complexes, such complexes would be very water insoluble and less hydrophilic. These kinds of hydrophobic complexes of the present invention would pass easier through biological membranes.

Other possibilities of polar complexes of the present invention may be, but are not limited to, lysophospholipids, phosphatidic acis, alkoxy compounds, glycerocarbohydrates, gangliosiedes, and cerebrosides.

Although there can be large structural differences between different compounds comprising non β-oxidizable fat acid entities of the present invention, the biological functions of all the compounds are expected to be very similar because they all block β-oxidation in the same manner. This inability of the fatty acid entities to be β-oxidized (and in some cases, ω-oxidized,) causes the analogues to build up in the mitochondria, which triggers the β-oxidation of the in vivo naturally occurring fatty acids, which in turn leads to many of the biological effects of the compounds comprising fatty acid entities of the present invention. (Berge R K et al. (2002) Curr Opin Lipidol 13(3):295-304)

The fatty acid β-oxidation pathway is the main pathway for the metabolism of fats. The initial and rate limiting reaction is carried out in the peroxisomes of the liver by acyl-CoA oxidase. Acyl-CoA oxidase catalyze the dehydrogenation of acyl-CoA thioesters to the corresponding trans-2-enoyl CoA. A fatty acid analogue according to formula (I); tetradecylthioacetic acid (TTA), has been used previously by the present inventors to test the various biological effects of the fatty acids. In the current invention, its effect on acyl-CoA oxidase was tested, as well as the effect of a protein material, alone or in concurrence.

The specific protein material tested herein is a fermented soy protein material. We are also in the process of testing a single cell protein material and a fish protein hydrolysate. Although these materials are complex and contain more than only protein, it is the protein part we believe act as the active ingredient, potentiating the beneficial effects of the non β-oxidizable fatty acids of the present invention. Based on the results with the fermented soy protein material disclosed herein, we expect similar results for the single cell protein material and the fish protein hydrolysate.

When testing for acyl-CoA oxidase activity TTA alone showed a large increase in activity compared to the negative control. The fermented soy protein material alone had almost no activity at all. But when TTA and the fermented soy protein material were used together, the acyl-CoA oxidase activity was more than doubled when comparing to the activity of TTA alone. This potentiating of TTA as an acyl-CoA oxidase activator by a fermented soy protein material is quite unexpected. It can certainly not be explained by an additive effect of TTA plus the fermented soy protein material; the unexpected synergistic effect is much too strong.

In the current invention, the effect of non β-oxidizable fatty acid entities on plasma phospholipids levels were also tested, as well as the effect of the fermented soy protein material, alone or in concurrence with TTA. TTA did lower the phospholipids level when compared to the control, while the fermented soy protein material actually increased the phospholipids levels somewhat. But when TTA and the fermented soy protein material were used together, the phospholipids level was, surprisingly, lowered beyond that of TTA alone. This potentiating of TTA as a plasma phospholipids lowering agent by a fermented soy protein material is quite unexpected. As with the acyl-CoA oxidase activity it can also not be explained by an additive effect of TTA plus the fermented soy protein material.

In the current invention, the effect of non β-oxidizable fatty acid entities on plasma cholesterol levels were also tested, as well as the effect of the fermented soy protein material, alone or in concurrence with TTA. The effects of fish oil were also tested, alone, with TTA, with the fermented soy protein material, or with both TTA and the fermented soy protein material. TTA alone showed a quite significant lowering of plasma cholesterol levels, and the fermented soy protein material or the fish oil alone also exhibited a cholesterol lowering effect. The fermented soy protein material and the fish oil also exhibited a cholesterol lowering effect greater than that of either separately. When fish oil or the fermented soy protein material was added to the TTA, the cholesterol lowering effect was surprisingly greater than that of TTA alone. When all three components; TTA, fish oil and the fermented soy protein material, were added at the same time, the cholesterol lowering effect was the greatest. This synergy between TTA, fish oil and the fermented soy protein material is quite unexpected.

TTA has been shown to reduce the plasma triglycerides level by increasing the number of mitochondria and stimulating mitochondrial β-oxidation of normal saturated and unsaturated fatty acids to ketone bodies (Froyland L et al. (1997) J Lipid Res 38:1851-1858). In the present invention, it was found that this effect was further unexpectedly potentiated by the addition the fermented soy protein material. In these experiments, the results for fermented soy protein were quite string and unexpected TTA did, as expected, lower the triglycerides level. The fermented soy protein alone actually increased the triglycerides level by 30% when compared to the control, but it still potentiated the triglycerides lowering effect of TTA by 50%. These synergistic effects are also very much unexpected.

In the present invention, the effect of feeding Atlantic salmon a feed comprising non β-oxidizable fatty acid analogues, common feed components and a fermented soy protein material was tested. In example 2.1, fish feed was composed from coating common feed pellets with fish oil including TTA and a fermented soy protein material. This feed was then used in example 2.2 as the food supply for Atlantic salmon, and the presence of TTA had beneficial effects on the thus produced compared to fish fed equivalent feed without TTA (examples 2.3 and 2.4).

The common feed pellets used comprised mostly fish meal, some wheat and a vitamin and mineral additive. The oil used for the coating of the pellets was of marine origin, from capelin, and had various amounts of TTA mixed in. Table 1 describes the formulation and chemical composition of the diets. This is a common feed, well suited for the test species (in this example Atlantic salmon), which upon addition of TTA exhibits beneficial effects. As shown previously in this application, TTA administered together with protein has an added beneficial effect as compared to TTA alone. The fact that this common feed is high in fats and protein and low in carbohydrates probably increased the beneficial effects of TTA over TTA being Ministered alone, or in a diet with more carbohydrates.

In example 2.4, the effects of a specific protein material, a fermented soy protein material, was ascertained. The fermented soy protein material is resulting from a fermentation of soy beans. It comprises modified and un-modified soy proteins and isoflavones, as well as other soy constituents. A preferred embodiment of the invention uses the fermented soy protein material GENDAXIN® (isoflavone concentrate) by aXiMed.

Table 2 describes the fatty acid composition of the diets. There were only minor differences in the fatty acid composition of the diets (all contained nearly 100% fish oil), the percentage of n-3 fatty acids (FA) was almost equal. Diets supplemented with TTA, however, led to substantial changes in the percentage of n-3 fatty acid composition of the phospholipids (PL), triacylglycerols (TAG) and free fatty acids (FFA) of gills, heart and liver of Atlantic salmon. Administration of TTA during the 8 weeks also resulted in a decreased percentage of saturated FAs in almost all the lipids fractions. The percentage of the n-3 FAs, especially DHA, increased in the gills and heart, as can be seen in example 2.3.

Atlantic salmon fed diets containing TTA grew at a slower rate than fish fed the control diet. The body lipid level it fish fed the diets supplemented with TTA was significantly lower than it was in fish fed the control diet.

There are health benefits to the fish itself by being fed a feed according to the invention. Old fish may experience arterial sclerosis and resulting health problems just like humans, and a lowering of lipids will hive a beneficial effect on this.

In general, lean meat, as obtained by the method of the present invention, is considered beneficial in most animal species reared for consumption. Thus the effect of lowering the total lipid levels is in itself advantageous. In addition, the specific changes in fatty acid composition are particularly positive. It is widely recognized that consuming less saturated fatty acids is healthy, and an increased consumption of n-3 has been associated with a whole host of health benefits, from reducing the chance of heart diseases to anti-inflammatory effects and even smarter babies.

Other animal products obtained from animals fed the feed of the present invention may also have beneficial effects. As an example would fish oil thus obtained have an advantageous nutritional composition when compared to oil from fish fed commercial diets. Other products, such as fish skins, may also have beneficial effects seeing as the whole body composition is improved.

The level of fatty acids in the blood is normally determined by the relative rates of lipolysis and esterification in adipose tissue, and the uptake of fatty acids in the muscles. In the muscles, fatty acids inhibit glucose uptake and oxidation. Increased levels of fatty acids and triacylglycerol in the blood and muscles therefore correlate with obesity and insulin resistance, as well as a reduced ability to metabolize glucose (Olefsky J M (2000) J Clin Invest 106:467-472; Guerre-Millo M et al. (2000) J Biol Chem 275:16638-16642). We have shown stimulation of fatty acid oxidation and decreased plasma fatty acid concentration obtained by non β-oxidizable fatty acid entities and a protein material, or optionally also comprising an oil component. We thus anticipate that the compositions of the present invention can be used to prevent and treat insulin resistance and diseases caused thereby (Shulman G I (2000) J Clin Invest 106(2):171-176). TTA has been found to completely prevent high-fat diet induced insulin resistance and adiposity, and reduce adiposity, hyperglycaemia and insulin sensitivity in obese mats (Madsen M et al. (2002) J Lipid Res 43(5):742-50). Due to the unexpected synergetic results found by the inventors using both TTA and a protein material, and optionally also oil, without being bound to any specific theory of why the results are as shown, we now expect that this combination will be even more effective in the treatment of these conditions. We also expect TTA to be potentiated by a protein material, and optionally also oil, in treating related diseases and disorders including elevated blood pressure, increased lipid and cholesterol levels, endothelial dysfunction, procoagulant state, polycystic ovary syndrome and the metabolic syndrome.

The peroxisome proliferator-activated receptor (PPAR) family are pleiotropic regulators of cellular functions such as cellular proliferation, differentiation and lipid homeostasis (Ye J M et al. (2001) Diabetes 50:411-417). The PPAR family is comprised of three subtypes; PPARα, PPARβ, and PPARγ. TTA is a potent ligand of PPARα (Forman B M, Chen J, Evans R M (1997) Proc Natl Acad Sci 94:4312-4317; Gottlicher M et al. (1993) Biochem Pharmacol 46:2177-2184; Berge R K et al. (1999) Biochem J 343(1):191-197), and activate PPARβ and PPARγ as well (Raspe E et al. (1999) J Lipid Res 40:2099-2110). As a PPARα activator TTA stimulate the catabolism of fatty acids by increasing their cellular uptake. Lowering the plasma triglyceride levels with TTA caused a shift in liver cellular metabolism, towards PPARα regulated fatty acid catabolism in mitochondria (Graf H J et al. (2003) J Biol Chem 278(33):30525-33) While the effect of TTA on plasma triacylglycerol is direct by PPARα activation, which is demonstrated by the abolishment of this effect in PPARα knockout mice, fish oil does reduce plasma triacylglycerol even in knockout mice (Dallongeville J et al. (2001) J Biol Chem 276:4634-4639).

Supplement with dietary n-3 poly unsaturated fatty acids like those found in fish oil stimulate hepatic peroxisomal acyl-CoA oxidase activity and thus fatty acid oxidation in the liver and to a smaller extent in skeletal muscle (Ukropec J et al. (2003) Lipids 38(10)1023-9). A fish oil rich diet has been shown to increase both the activity and mRNA levels of hepatic mitochondrial and peroxisomal fatty acids oxidation enzymes (Hong D D et al. (2003) Biochim Biophys Acta: Mol Cell Biol Lipids 1635 (1):29-36). Fish oil induced an increase in abundance of peroxidal acyl-CoA oxidase in the liver but not muscles of rats, and the authors hypothesise that this is due to n-3 fatty acids protect against fat-induced insulin resistance by serving a PPARα ligands, inducing hepatic (not intramuscular) peroxisome proliferation. PPARα gene expression did not change. (Neschen S et al. (2002) Am J Physiol Endocrinol Metab 282:E395-E401)

As can be seen in the above paragraphs, the biochemical details of exactly how TTA, a protein material, and optionally oil influence fat metabolism are not known in detail. The effects may or may not be through the same paths, both TTA and oils may for instance act as PPARα ligands, or independently of PPARα. If they work through the same paths, one would not expect TTA to be potentiated by the oils, because TTA is a strong PPARα activator which one would expect would fully saturate the PPARα activation. To even get an additive effect of the TTA effect plus the oil when combining them would then be unexpected. Even less is known of how protein influence β-oxidation or other aspects of fat metabolism. Thus one cannot predict the effects of administering both a protein material and TTA at the same time. However, to get a synergistic effect way above the additive effect, as is seen for TTA and the fermented soy protein material in all tests of the present invention, is very surprising. β-oxidizable fatty acid entities have many effects, and we do not know how they are all brought about, but based upon the unexpected results of the present invention we expect them all to be potentiated by protein materials and optionally oils without being bound to any specific theory.

PPAR ligands affect proliferation of various cancer cell lines. TTA in particular has been found to reduce proliferation of many cancer cell lines (Berge K et al. (2001) Carcinogenesis 22:1747-1755; Abdi-Dezfuli F et al. (1997) Breast Cancer Res Treat 45:229-239; Tronstad K J et al. (2001) Biochem Pharmacol 61:639-649; Tronstad K J et al. (2001) Lipids 36:305-313). This reduction is related to reduction in triacylglycerol levels (Tronstad K J et al. (2001) Biochem Pharmacol 61:639-649), and is mediated by both PPAR dependent and independent pathways (verge K et al. (2001) Carcinogenesis 22:1747-1755). Since fermented soy protein improve TTA's ability to lower triacylglycerol levels, it is therefore highly likely that it will improve the anti-proliferative effects of TTA as well, making this an improvement upon TTA's cancer prevention and treatment abilities. TTA may be used for the prevention and/or treatment of cancer including inhibition of: primary and secondary neoplasms, the growth of tumours, invasion of a primary tumour into connective tissue and formation of secondary tumours (NO 2002 5930).

In general, PPAR agonists modulate the inflammatory response. TTA modulate inflammatory response by depressing the release of inflammatory cytokine interleukin-2 and suppressing PHA stimulated proliferation of peripheral mononuclear cells (Aukrust P et al. (2003) Eur J Clin Invest 33(5):426-33). The modulation of cytokine by TTA may be PPAR mediated or through altered prostaglandin levels or by modification of lipid mediated signal transduction, the latter which also is the proposed mechanism of action for poly unsaturated fatty acids, as those found in oils. Now that the inventors have found the unexpected results of the present invention, they therefore expect hat protein material, and optionally oil, in combination with non β-oxidizable fatty acid entities will potentiate the effect of the fatty acid entities on inflammatory disorders, including immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegener's granulomatosis), inflammatory bowel diseases, Chron's disease, non specific colitis, pancreatitis, nephritis, cholestatis/fibrosis of the liver, and acute and chronic allograft rejection after organ transplantation, as well as proliferate skin disorders like psorasis, atopic dermatitis, non-specific dermatitis, primary irritant contact-dermatitis, allergic contact-dermatitis, lamellar ichthyosis, epidermolytic hyperkeratoses, pre-malign sun-induced keratoses, and seborrhoea, and diseases that have an inflammatory component such as e.g. Alzheimer's disease or impaired/improvable cognitive function.

FIGURE LEGENDS

FIG. 1 shows that the increase in fatty acyl-CoA activity by TTA is potentated by fermented soy protein material.

FIG. 2 shows that the phospholipids lowering effect of TTA is potentated by fermented soy protein material.

FIG. 3 shows that the cholesterol lowering effect of TTA is potentated by fermented soy protein material and fish oil.

FIG. 4 shows that the triacylglycerol lowering effects of TTA is potentated by fermented soy protein material.

DEFINITIONS USED IN THE APPLICATION

Animals

In this context the term "animals" include mammals such as humans and farm (agricultural) animals, especially the animals of economic importance such as gallinaceous birds, bovine, ovine, caprine and porcine mammals, especially those that produce products suitable for the human consumption, such as meat, eggs and milk. Further, the term is intended to include fish and shellfish, such as salmon, cod, Tilapia, clams, oysters, lobster or crabs. The term also includes domestic animals such as dogs and cats.

Animal Feed

The term animal feed refers to food for animals (as defined above). Animal feed usually comprise appropriate amounts of fats, proteins, carbohydrates, vitamins and minerals necessary for the sustenance of the intended animal recipient, and may comprise additional components for the improvement of taste, texture, colour, smell, stability, storage life etc, or antibiotics or other components added for the benefit of the health of the animal. The animal feed is preferably but not necessary dry matter, most preferably a pellet material. The term animal feed is also intended to include nutritional compositions, veterinary compositions, and/or functional food products for animal consumption.

Meat

The word meat refers to flesh from any-animal as defined above. Thus, the protein containing flesh from mammals, birds, fish and shellfish is all referred to as meat. The term "meat product" refers to any product produced from meat as defined above.

Plant and/or Fish Oils

These include all oils of plant or marine origin, including but not limited to fatty or fixed oils as well as essential or volatile oils, and any combination thereof. They do not necessarily need to be in liquid form. Sunflower oil, which was used in the present invention, is really oil from the sunflower seed, not the flower itself.

Fish Oil

This term include all oils of a marine origin.

Nutritional Composition

This term is meant to include any ingestible material, including but not restricted to nutritional supplements, frictional foods, herbal supplements etc. for human or animal consumption. The term also includes food products for human consumption and animal fodder, wherein the composition of the present invention is an additive, and not the main ingredient. This especially concerns animal fodder, where any fodder can be supplemented with the composition of the present invention, to attain the biological effects thereof.

Treatment

In relation to the pharmaceutical applications of the invention the term "treatment" refers to a reduction of the severity of the disease.

Prevention

The term "prevention" refers to the preventing of a given disease, i.e. a compound of the present invention is administered prior to the onset of the condition. This means that the compounds of the present invention can be used as prophylactic agents or as ingredients in a nutritional composition in order to prevent the risk or onset of a given disease.

Fermentation

The decomposition of organic substances by microorganisms or enzymes, including hydrolyzation.

Hydrolyzation

Enzymatic or chemical decomposition where complex molecules are split into simpler units by a chemical reaction with water.

Single-cell Protein Material (SCP)

SCP is a material comprising single-cell microorganisms. The microorganisms can inter alia be fungi, yeasts and bacteria. The SCP material contains high proportions of proteins.

Enzyme Treated Fish Protein Hydrolysate (FPH)

The FPH material is a protein hydrolysate resulting from all enzymatic treatment of a fish material. The FPH material contains high proportions of proteins and peptides.

Fermented Soy Protein Material

The fermented soy protein material is resulting from a fermentation of soy beans. It comprise modified and unmodified soy proteins and isoflavones, as well as other soy constituents.

Nutritional Composition

This term is meant to include any ingestible material, including but not restricted to nutritional supplements, functional foods, herbal supplements etc. for human or animal consumption. The term also includes food products for human consumption and animal fodder, wherein the composition of the present invention is an additive, and not the main ingredient. This especially concerns animal fodder, where any fodder can be supplemented with the composition of the present invention, to attain the biological effects thereof.

ADMINISTRATION OF THE COMPOUNDS OF THE PRESENT INVENTION

As a pharmaceutical medicament the composition of the present invention may be administered directly to the animal by any suitable technique, including parenterally, intranasally, orally, or by absorption through the skin. They can be administered locally or systemically. The specific route of administration of each agent will depend, e.g., on the medical history of the recipient human or animal.

Examples of Parenteral Administration Include Subcutaneous, Intramuscular, Intravenous, Intra-Arterial, and Intra-Peritoneal Administration As a general proposition, the total pharmaceutically effective amount of each of the non $\beta$-oxidizable fatty acid entities administered parenterally per dose will preferably be in the range of about 1 mg/kg/day to 200 mg/kg/day of patient body weight for humans, although, as noted above, this will be subject to a great deal of therapeutic discretion. A dose of 5-50 mg/kg/day is most preferable. A dose of 5-500 mg/kg/day of fermented soy protein material or other protein material is preferable, and a dose of 50-300 mg/kg/day is most preferable. A dose of 1-300 mg/kg/day of fish oil or other oil is preferable, and a dose of 10-150 mg/kg/day of fish oil or other oil is most preferable.

If given continuously, the compounds of the present invention are each typically administered by 1-4 injections per day or by continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner.

For parenteral administration, in one embodiment, the compounds of the present invention are formulated generally by each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the compounds of the present invention each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Nonaqueous vehicles such as fixed oils and ethyl oleate are also useful herein, as well as liposomes.

The carrier may suitably contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

For oral pharmacological compositions such carrier material as, for example, water, gelatine, gums, lactose, starches, magnesiun-stearate, talc, oils, polyalkene glycol, petroleum jelly and the like may be used. Such pharmaceutical preparation may be in unit dosage form and may additionally contain other therapeutically valuable substances or conventional pharmaceutical adjuvants such as preservatives, stabilising agents, emulsifiers, buffers and the like. The pharmaceutical preparations may be in conventional liquid forms such as tablets, capsules, dragees, ampoules and the like, in conventional dosage forms, such as dry ampoules, and as suppositories and the like.

In addition the compounds of the present invention, i.e. the $\beta$-oxidizable fatty acid analogue and protein material, or the $\beta$-oxidizable fatty acid analogue and protein material and oil, may be used in nutritional preparations, as defined earlier, in which case the dosage of non $\beta$-oxidizable fatty acid analogue preferable is as described pharmaceuticals or less, while the amounts of protein material and oil preferably are suitable for the preparation of food and feed materials. As a part of a nutritional composition, and especially animal fodder, the oil and protein material can be a substantial part of the fodder, and thus have a nutritional value as well as potentiating the non $\beta$-oxidizable fatty acid analogues. Fish oil can comprise up to all of the fat in a nutritional composition, and fermented soy protein material can comprise up to all of the protein in a nutritional composition. In animal fodder, the amount of non $\beta$-oxidizable fatty acid analogue can be up to 10 ties that in products for human consumption, that is, up to 2 g/kg/day of animal body weight Such animal fodder may be used for routine feeding of animals. Fermented soy protein material is especially useful as a functional protein in food products, particularly when used as a substitute for natural plasma in animal feeds and in pet foods. An animal feed composition may also comprise additional ingredients such as fats, sugars, salt, flavourings, minerals, etc. The product may then be formed into chunks resembling natural meat chunks in appearance and texture. The product of the invention has the further advantages that this is readily formulated to contain necessary nutrients, is easily digested by the animals and is palatable to the animals.

Experimental Section

The preparation of non $\beta$-oxidizable fatty acid entities according to the present invention is disclosed in detail in the applicant's earlier Norwegian patent applications no. 20005461, 20005462, 20005463 and 20024114. These documents also describe toxicity studies of TTA. Preparation of mono-, di-, and triglycerides and nitrogen comprising lipids according to the invention is disclosed in detail in U.S. patent application Ser. No. 10/484,350. The preparation of phospholipids including serine, ethanolamine, choline, glycerol, and inositol according to the invention is disclosed in detail in the applicant's earlier Norwegian patent application no. 20045562.

The experimental results given below have revealed that protein material and/or oil substantially potentiate the biological effects non β-oxidizable fatty acid analogues.

EXAMPLE 1

Biological Effects in Rats of the Composition According to the Invention 1.1 Preparation of Fish Protein Hydrolysate (FPH)

Starting Materials

FPH was produced from fish flesh remnants on salmon bone frames after filleting. Frames without heads or freshly filleted Atlantic salmon (*Salmon Salar, L.*) were taken directly from the production line and frozen at −20±2° C.: Within a week the frozen frames were used in the enzymatic hydrolyzing process.

Hydrolysis

The enzymatic hydrolysis was performed with Protamex™ at a pH of about 6.5 and at a temperature of 55±2° C. Protamex™ (E.C. 3.4.21.62/3.4.24.28)is a *Bacillus* protease complex from Novozymes AS (Bagsvaerd, Denmark) and fulfils the purity demands for food-grade enzymes. The ratio of salmon frames to water was 1.14. An enzyme to substrate ratio of 11.1 AU/kg crude protein was used in the hydrolysis. After 60 min of enzymatic treatment the temperature was elevated to 98° C., which was reached after 105 min.

Purification

Large bones were retained in the hydrolysing tank, while small bones were removed by filtering the hydrolysate trough a mesh. Thereafter the insoluble fraction was removed in a two-phase separator (Westfalia, Germany, SC.35-26-177, 15 kW, 7200 rpm), before the remaining mixture was separated in a three-phase separator (Westfalia, Germany, SB-7-36-+ 76, 4 kW, 8520 rpm) into salmon oil, emulsion fraction and aqueous fraction. The aqueous fraction was concentrated (NitroAtomicer, Denmark, Falling Film Evaporator, Ff 100), filtered through an ultra-membrane with nominal molecular weight limit of 100 000 (PCI membrane Systems, UK, PF100, 2.65 m$^2$) and finally the ultra-membrane filtered fraction (UF fraction) was spray-dried (Niro Atomizer, Denmark, P-63 tower, $T_{in}$=200° C., $T_{out}$=84° C.).

Final Product

The UF fraction is termed fish protein hydrolysate (FPH). The FPH material contains about 83% protein, 10% ash and about 2% lipids, based on dry weight. Further characterising of the FPH can be found in the applicants prior application NO 2003 3078. The synthesis of the FPH was given as an example, not to illustrate the synthesis of all protein materials or even fish protein hydrolysates of formula (I).

1.2 Preparation of Single-cell Protein (SCP) Material

Starting Materials

A microbial culture comprising *Methylococcus capsulatus* (Bath), *Ralstonia* sp., *Brevibacillus agri* and *Aneurinibacillus* sp, all commercially available from Norferm Denmark AS, Odense, Denmark is produced in a loop-type fermentor by continuous aerobic fermentation of natural gas in an ammonium/mineral salts medium (AMS) at 45 C, pH 6.5, and at a dilution rate of 0.15 h$^{-1}$. The AMS medium contains the following per liter: 10 mg $NH_3$, 75 mg $H_3PO_4.2H_2O$, 380 mg $MgSO_4.7H_2O$, 100 mg $CaCl_2.2H_2O$, 200 mg $K_2SO_4$, 75 mg $FeSO_4.7H_2O$, 1.0 mg $CuSO_4.5H_2O$, 0.96 mg $ZnSO_4.7H_2O$, 120 μg $CoCl_2.6H_2O$, 48 μg $MnCl_2.4H_2O$, 36 μg $H_3BO_3$, 24 μg $NiCl_2.6H_2O$ and 1.20 μg $NaMoO_4.2H_2O$.

Production

The fermentor is filled with water which has been heat-sterilized at 125° C. for 10 sec. Addition of the different nutrients is regulated according to their consumption Continuous fermentation is operated with 2-3% biomass (on a dry weight basis).

A single-cell material is continuously harvested and subjected to centrifugation in an industrial continuous centrifuge at 3,000 rpm, followed by ultra filtration using membranes having an exclusion size of 100,000 Daltons. The resulting product is then subjected to sterilization in a heat exchanger at about 130° C. for about 90 seconds.

Further characterising of the SSP can be found in the applicants prior application NO 2003 3082. The synthesis of the SSP was given as an example, not to illustrate the synthesis of all protein materials or even single cell protein materials of formula (I).

1.3 Fermented Soy Protein Material

The fermented soy protein material is resulting from a fermentation of soy beans. It comprise modified and unmodified soy proteins and isoflavones, as well as other soy constituents. A preferred embodiment of the invention uses the fermented soy protein material Gendaxin®, commercially available from Aximed, Bergen, Norway. Gendaxin® is given as an example, not to illustrate all protein materials or even fermented soy protein materials of formula (I).

1.4 Biological Effects on Rats of the Composition According to the Invention

Chemicals

Chemicals were obtained from common commercial sources and were of reagent grade. Carboxymethylcellulose (CMC) was used as a control (negative). The fish oil was commercially available from Hordafor.

Animals

Male Wistar rats weighing from 250 to 358 g, were bought from AnLab Ltd. (Prahg, The Check Republic.), and were kept in wire cages in a temperature of 22±1° C. and light controlled (light from 7 am to 7 pm) room. There were no restrictions put on food and water intake. Three rats were kept in each cage. Increase in weight and food intake was monitored daily.

Diets

The rats were fed a standard Chow ST1 diet (from Velaz, Prahg, The Check Republic).

Treatments

Male Wistar rats were allowed to acclimatize to the new surroundings before initiation of the experiment. They were then treated daily for 10 days by gavage. CMC was used as a carrier and negative control. Each treatment group numbered 4 rats. The groups that were treated with TTA were given 150 mg/kg body weight/day dissolved in CMC or oils. The groups that were treated with fish oil were given 3 mL(ca 2.5 g)/kg body weight/day. The groups that were ted with fermented soy protein material were given 0.45 g/kg body weight/day. CMC was used as a carrier and negative control. The day after the last treatment the rats were sacrificed.

Sacrifice and Tissue Retrieval

The rats were anaesthetized with a 1:1 mixture of Hypnorm™ (fentanyl citrate 0.315 mg/ml and fluanisone 10 mg/ml, Janssen Animal Health) and Dormicum® (midazolam 5 mg/ml, F. Hoffmann-La Roche) injected subcutaneously. Blood was drawn directly from the heart using a heparin rinsed syringe. The liver was immediately removed, weighed and divided into two parts, which were immediately chilled on ice or frozen in liquid nitrogen, respectively. Plasma and tissues were stored at −80° until analysis. The protocol was approved by the Norwegian State Board of Biological Experiments with Living Animals.

Preparation of Hepatic Subcellular Fractions

Livers from the rats were homogenised individually in ice-cold sucrose-solution (0.25 mol/L sucrose in 10 mmol/L HEPES buffer pH 7.4 and 1 mmol/L EDTA) using a Potter-Elvehjem homogeniser. Subcellular fractionation of the livers was performed as previously described (Berge R K et al. (1984) Eur J Biochem 141: 637-44). The procedure was performed at 0-4° C., and the fractions were stored at −80° C. Protein was assayed with the BioRad protein assay kit using bovine serum albumin as the standard.

Enzyme Assay

Fatty acyl-CoA oxidase activity was measured in the peroxisomal liver fraction as previously described (Small G M, Burdett K, Connock M J (1985) Biochem J 227: 205-10). The results were given as fatty acyl-CoA oxidase activity per total protein, baseline activity (activity of control) was subtracted, and the data which is presented in FIG. 1 were normalized to the activity of TTA Lipid Analysis Plasma and liver lipids were measured enzymatically on the Technicon Axon system (Miles, Tarrytown, N.Y.) using the Triglyceride kit from Bayer, Total cholesterol (Bayer, Tarrytown, N.Y.), and the PAP150 kit for choline containing phospholipids from bioMerieux. The results were given per total protein, and the data which is presented in FIGS. 2-4 were normalized to the activity of the positive control (no added TTA or oils; i.e. "normal" levels). The results were given per total protein, and the data which is presented in FIGS. 2-4 were normal to the activity of the positive control (no added TTA or oils; i.e. "normal" levels).

EXAMPLE 2

Biological Effects in Atlantic Salmon of the Composition According to the Invention 2.1 Experimental Setup Including Preparation of the Fish Feed The experimental fishmeal-based diets were provided by EWOS and contained 0.01% $Y_2O_3$ as an inert marker for digestibility determination (3 mm pellets). Table 1 shows the formulations and chemical compositions of the three diets. All the three diets were produced from one feed mix. The different diets were obtained by coating the common feed pellet with the different oils and mixtures. The diets contained either fish oil (capelin oil) (Control), fish oil supplemented with 0.5% TTA (0.5% TTA) or fish oil supplemented with 1.5% TTA (1.5% TTA).

TABLE 1

Formulation and chemical composition of the diets
Diets: fish oil (Control), fish oil added 0.5% TTA (0.5% TTA), fish oil added 1.5% TTA (1.5% TTA).

|  | Control | 0.5% TTA | 1.5% TTA |
|---|---|---|---|
| Formulation (% of total) | | | |
| Fish meal, LT | 67.8 | 67.8 | 67.8 |
| Capelin oil[a] | 21.3 | 21 | 20.7 |
| TTA |  | 0.1 | 0.3 |

TABLE 1-continued

Formulation and chemical composition of the diets
Diets: fish oil (Control), fish oil added 0.5% TTA (0.5% TTA), fish oil added 1.5% TTA (1.5% TTA).

|  | Control | 0.5% TTA | 1.5% TTA |
|---|---|---|---|
| Wheat | 10.4 | 10.4 | 10.4 |
| Astax[b]-Cantax[c] | 0.06 | 0.06 | 0.06 |
| Mineral/Vitamin premix | 0.49 | 0.49 | 0.49 |
| Yttrium oxide | 0.01 | 0.01 | 0.01 |
| Chemical composition | | | |
| Dry matter (%) | 97.1 | 96.1 | 93.8 |
| Protein (%) | 51.9 | 51.4 | 49.7 |
| Fat (%) | 26.9 | 26.7 | 26.7 |
| Ash (%) | 10.8 | 10.4 | 10 |
| Energy (MJ/kg) | 23.8 | 23.7 | 23.2 |

[a]Capelin oil, Norsildmel, Norway.
[b]Asta, BASF, lucanthin red.
[c]Canta, lucanthin pink.

The fatty acid composition of the diets clearly reflected that of the fish oil used (capelin oil) (Table 2). The capelin oil contained relatively high levels of the monounsaturated FAs and was also rich in the long-chain n-3 FAs, 20:5 n-3 (EPA) and 22:6 n-3 (DHA). The feed, however, contained a significant amount of fish meal, which contained n-3 FAs, ensuring that the levels of these FA in the diet where higher than those in the added oil.

In addition to the above diets, identical diets but with 0.5% Gendaxin and 0% or 0.9% TTA (based on the total dry weight of the feed) were prepared.

TABLE 2

Fatty acid composition of the diets

| Fatty acids | Control | 0.5% TTA | 1.5% TTA |
|---|---|---|---|
| 12:0 | 0.1 | 0.1 | 0.1 |
| 14:0 | 6.7 | 6.6 | 6.6 |
| 15:0 | 0.3 | 0.3 | 0.3 |
| 16:0 | 11.8 | 11.6 | 11.5 |
| 16:1 n − 7 | 7.1 | 7 | 6.9 |
| 16:1 n − 9 | 0.4 | 0.3 | 0.3 |
| 16:2 n − 7 | 0.4 | 0.4 | 0.4 |
| 17:0 | 0.1 | 0.1 | 0.1 |
| 18:0 | 1.4 | 1.3 | 1.3 |
| 18:1 n − 6 | 0.4 | 0.4 | 0.4 |
| 18:1 n − 7 | 3.1 | 3 | 3 |
| 18:1 n − 9 | 11.5 | 11.6 | 11.3 |
| 18:2 n − 6 | 2.7 | 2.7 | 2.6 |
| 18:3 n − 6 | 0.1 | 0.1 | 0.1 |
| 18:3 n − 3 | 0.7 | 0.7 | 0.7 |
| 18:4 n − 3 | 2.1 | 2.1 | 2.1 |
| TTA |  | 0.5 | 1.5 |
| 20:0 | 0.1 | 0.1 | 0.1 |
| 20:1 n − 9 | 0.5 | 0.5 | 0.5 |
| 20:1 n − 11 | 17.9 | 17.9 | 17.7 |
| 20:2 n − 6 | 0.2 | 0.2 | 0.2 |
| 20:3 n − 3 | nd | nd | nd |
| 20:4 n − 3 | 0.4 | 0.4 | 0.4 |
| 20:4 n − 6 | 0.3 | 0.3 | 0.3 |
| 20:5 n − 3 | 5.9 | 5.9 | 5.8 |
| 22:0 | 0.2 | nd | nd |
| 22:1 n − 9 | 1.9 | 1.9 | 1.8 |
| 22:1 n − 11 | 14.1 | 14 | 14 |
| 22:2 n − 6 | 0.1 | 0.2 | 0.2 |
| 22:5 n − 3 | 0.5 | 0.4 | 0.5 |
| 22:6 n − 3 | 6.4 | 6.2 | 6.2 |
| Σ Saturates | 20.7 | 20.1 | 20 |

TABLE 2-continued

Fatty acid composition of the diets

|  | Control Fatty acids | 0.5% TTA | 1.5% TTA |
|---|---|---|---|
| Σn – 3 | 15.9 | 15.7 | 14.1 |
| Σn – 6 | 3.5 | 3.5 | 3.4 |

Control: fish oil, 0.5% TTA: fish oil added 0.5% TTA, 1.5% TTA: fish oil added 1.5% TTA. The quantity of each fatty acid is given as a percentage of the total fatty acids.

2.2: Rearing Atlantic Salmon on Feed Comprising TTA

Fish, Facilities and Experimental Design

The trial was conducted at AKVAFORSK Research Station, Sunndalsøra, Norway. Atlantic salmon (*Salmon salar*) with a mean initial weight of approximately 86 g were placed into 15 cylinder-conical tanks (0.85 m diameter), 40 fish per tank. The tanks were supplied with seawater with a constant temperature of 12° C. The fish were acclimatised to the temperature and fed a commercial feed for two weeks before the start of the trial. The growth trial consisted of one period of 8 weeks.

The diets were as described above in table 2, containing either fish oil (capelin oil) (Control), fish oil supplemented with 0.5% TTA (0.5% TTA) or fish oil supplemented with 1.5% TTA (1.5% TTA). The tree diets were randomly assigned to triplicate tanks. The feed was distributed by electrically driven disc-feeders (Akvaprodukter AS, Sunndalsøra). The tanks were designed such that waste feed was collected from the effluent water in wire mesh boxes. Wasted feed was collected, and this allowed the weight of feed consumed to be calculated.

The Gendaxin containing diets were used in a separate experiment, but the design thereof was the same as described above.

Initial and Final Sampling

The fish were fasted for 2 days before the initial sampling. Six fish from each tank were anaesthetised in MS-222 at the beginning and at the end of the experiment, and the mean weight and mean length were determined. These six fish were killed by a blow to the head and the abdomen cut open. Samples of liver, heart, gills and kidney were immediately frozen in liquid nitrogen and stored at –80° C. These samples were subsequently used for the analysis of fatty acid composition. A further five fish per tank were anaesthetised and killed. These fish were used for determination of the composition of the whole body.

The fish were not fasted before the final sampling. Five fish from each tank were stripped to collect faecal samples following the procedure described by Austreng (*Aquaculture*, 1978 13:265-272). Faecal samples from each tank were pooled. The samples were stored at –20° C. prior to analyses.

The second gill arch was removed from anaesthetised fish and rinsed in ice-cold SEI buffer (150 mM sucrose, 10 nM EDTA, 50 mM imidazole, pH 7.3) and immediately frozen in liquid nitrogen. Gill tissues were stored at –80° C. Livers were homogenized in ice-cold sucrose medium.

Growth

The mean weight of the fish nearly tripled during the trial, in al dietary groups, from an initial value of 86 g to a final value of approximately 250 g. The SGRs decreased with increasing dietary doses of TTA, from and SGR of 1.8 in the control group to an SGR of 1.7 in the 0.5% TTA group and an SGR of 1.5 in the 1.5% TTA group (Table 3). There were no significant differences in the condition factor between the dietary groups Table 3).

TABLE 3

Effect of dietary inclusion of TTA and oil on feed intake and growth on Atlantic salmon

|  | Control | 0.5% TTA | 1.5% TTA |
|---|---|---|---|
| Initial weight | 85 ± 2 | 88 ± 1 | 86 ± 2 |
| Final weight | 278 ± 7 | 267 ± 3 | 233 ± 1 |
| CF | 1.2 ± 0.02 | 1.1 ± 0.02 | 1.2 ± 0.02 |
| TGR | 2.6 ± 0.44$^c$ | 2.5 ± 0.05$^b$ | 2.0 ± 0.06$^a$ |
| SGR | 1.8 ± 0.02$^c$ | 1.7 ± 0.03$^b$ | 1.5 ± 0.05$^a$ |
| Total FER | 1.2 ± 0.05 | 1.2 ± 0.04 | 1.1 ± 0.12 |

Values are means ± SEM (n = 3)
CF (%): Condition factor, SGR: Specific growth rate, TGC: Thermal growth coefficient, FER: Feed efficiency ratio (wet gain/dry feed intake).
$^{abc}$Differences between mean values within a given row are significant (p ≤ 0.05), as indicated by different superscript letters.

Feed Intake and Nutrient Digestibility

There were only small differences in digestibility in this trial (Table 4). The digestibilities of FAs in all dietary groups were high, being greater than 96% for the sum of all FAs for the fish fed the control diet and the 0.5% TTA diets, and greater than 90% for the fish fed the 1.5% TTA diet. The digestibilities of the saturated FAs were, in general, lower than those for the other FAs.

TABLE 4

Nutrient digestibility in Atlantic salmon

|  | Control | 0.5% TTA | 1.5% TTA |
|---|---|---|---|
| Energy | 89.5 ± 0.08 | 89.0 ± 0.58 | 87.1 ± 1.22 |
| Protein | 87.7 ± 0.15 | 87.9 ± 0.31 | 87.5 ± 0.44 |
| Fat | 97.3 ± 0.58 | 96.5 ± 1.27 | 94.9 ± 2.12 |
| ΣSaturated | 93.2 ± 1.54$^b$ | 81.4 ± 1.95$^a$ | 81.5 ± 2.18$^a$ |
| ΣMonounsaturated | 87.8 ± 5.66 | 90.4 ± 5.56 | 95.4 ± 1.87 |
| ΣPolyunsaturated | 90.9 ± 7.77 | 94.0 ± 4.45 | 92.5 ± 5.08 |
| TTA |  | 98.6 ± 0.45 | 97.0 ± 1.59 | of protein, fat, energy content and selected fatty acid in Atlantic salmon fed diets containing Control: fish oil, 0.5% TTA: fish oil added 0.5% TTA, 1.5% TTA: fish oil added 1.5%
Data are % means ± SEM
Values within the same row with different superscripts are significantly different;
nd = not detectable.

2.3 Biological Effects of TTA

Chemicals

Acetic acid, chloroform, petroleum ether and methanol were all obtained from Merck (Darmstadt, Germany). Benzene was obtained from Rathburn Chemicals Ltd. (Walkerburn, Scotland) and 2',7'-dichlorofluorescein from Sigma Chemical Co. (St. Louis, Mo., USA). Methanolic HCl and 2,2-dimethoxypropane was purchased from Supelco Inc. (Bellfonte, Pa., USA). Glass-baked silica gel K6 plates were obtained from Whatman International Ltd. (Maidstone, England).

Chemical Analysis

Fish sampled at the beginning and at the end of the experiment were analysed for dry matter, fat, protein, ash and energy content. All diets and faecal samples were analysed for dry matter (by drying at 105° C. to constant weight), fat (by ethyl-acetate extraction as described in NS 9402, 1994), protein (by a Kjeltec Autoanalyser-N*6.25), starch, ash (by heating to 550° C. until constant weight), energy and yttrium oxide (using ICP-AES after wet ashing the samples). The energy contents of the diets, faeces and whole fish samples were determined by adiabatic bomb calorimetry, using a Parr 1271 Bomb Calorimeter.

Lipid Extraction and Fatty Acid Analysis

Total lipids were extracted from homogenised gills, liver and heart using the method described by Folch (*J Biol Chem* 1957 226:497-509). The chloroform-methanol phases from the gills were dried under nitrogen and dissolved in hexane. Phospholipids (PL), triacylglycerol (TAG) and free fatty acids (FFA) were separated by thin-layer chromatography (TLC) using a mixture of petroleum ether, diethyl ether and acetic acid (113:20:2 by volume) as the mobile phase. The lipids were visualised by spraying the TLC plates with 0.2% (w/v) 2',7'-dichlorofluorescein in methanol and they were identified by comparison with known standards under UV-light The spots corresponding to PL, FFA, and TAG were scraped off into glass tubes and were then trans-methylated overnight with 2,2-dimethoxypropane, methanolic-HCL and benzene at room temperature as described by Mason and Waller (*Anal Chem* 1964 36:583). The methyl esters were separated on a non-polar fused capillary column by gas chromatography basically as described by Røsjø (*Fish Physiol Biochem* 1994 13:119-132). The methyl esters of FAs were separated in a gas chromatograph (Perkin-Elmer Auto system GC equipped with an injector, programmable split/splitless injector) with a CP wax 52 column (with lengh 25 m, internal diameter 0.25 mm and tickness of the film 0.2 μm), flame ionisation detector and 1022 data system. The carrier gas was He, and the injector and detector temperatures were 280° C. The oven temperature was raised from 50° C. to 180° C. at the rate of 10° C. min$^{-1}$, and then raised to 240° C. at the rate of 0.7° C. min$^{-1}$. The relative quantity of each fatty acid present was determined by measuring the area under the peak corresponding to that fatty acid Calculations Apparent digestibility coefficients (ADC) were calculated as described by Austreng (*Aquaculture*, 1978 13:265-272). Condition factor (CF), hepatosomatic index (HSI), specific growth factor (SGR) and thermal unit growth coefficient (TGC) were calculated as follows based on individual recordings of weights and lengths:

$$SGR = (e^{(\ln W_1 - \ln W_0)/days} - 1) * 100$$

$$TGC = (W_1^{1/3} - W_0^{1/3}) * 1000 / (days *° C.)$$

where $W_0$ is initial weight, $W_1$ is final weight, and t day degrees.

$$CF = 100 * W * (\text{fork length})^{-3}$$

$$HSI = 100 * \text{liver weight} * W^{-1}$$

Statistical Analysis

All data was subjected to one-way analysis of variance (ANOVA) and differences were ranked by Duncan's multiple range test. The significance level was set at 5%.

Body and Liver Composition

Fish fed the 1.5% TTA diet had a lower body lipid level (9.6%) than fish fed the control diet (10.6%) (Table 5). No statistically significant differences were found in the total liver lipid content between fish fed the control diet and fish fed the TTA diets (Table 6). The hepatosomatic index was significantly higher in fish fed the 1.5% TTA diet (1.2%) than in fish fed the control diet (1.1%) diet (Table 6).

TABLE 5

Chemical composition of the carcass in % of wet weight basis

|  | Start | Control | 0.5% TTA | 1.5% TTA |
|---|---|---|---|---|
| Crude lipid (%) | 8.3 | 10.6 ± 0.01$^b$ | 11.0 ± 0.42$^b$ | 9.6 ± 0.09$^a$ |
| Crude protein (%) | 16.8 | 18.1 ± 0.06 | 17.8 ± 0.19 | 18.0 ± 0.22 |
| Dry matter (%) | 27.6 | 31.1 ± 0.12$^b$ | 31.0 ± 0.15$^b$ | 29.9 ± 0.10$^a$ |
| Ash (%) | 2.3 | 2.0 ± 0.05 | 2.0 ± 0.02 | 2.0 ± 0.06 |
| Energy (MJ/Kg) | 7.1 | 8.5 ± 0.03$^b$ | 8.5 ± 0.10$^b$ | 8.0 ± 0.05$^a$ |

Control: fish oil, 0.5% TTA: fish oil added 0.5% TTA, 1.5% TTA: fish oil added 1.5% TTA.

$^{ab}$Differences between mean values within a given row are significant (p ≤ 0.05), as indicated by different superscript letters.

TABLE 6

Effect of dietary inclusion of TTA and oils on hepatosomatic index (HSI) and liver lipid content

|  | Control | 0.5% TTA | 1.5% TTA |
|---|---|---|---|
| HIS | 1.1 ± 0.01$^a$ | 1.1 ± 0.02$^a$ | 1.2 ± 0.03$^b$ |
| Liver lipid content (%) | 4.9 ± 0.27 | 5.1 ± 0.12 | 5.7 ± 0.69 |

Results are means ± SEM (n = 3).

Values within the same row with different superscript are significantly different.

Fatty Acid Compositions of Liver, Gills and Heart

The fatty acid compositions of PL, TAG and FFA of gills, liver and heart are shown in Tables 7, 8 and 9. TTA was incorporated into the PL fraction of the gills (0.8%) and heart (0.7%) of the Atlantic salmon fed the 1.5% TTA diet. TTA was also incorporated into the TG and the FFA fractions of the gills (Table 7). Traces of TTA and its Δ$^9$ desaturase products were incorporated into the liver lipids, while no Δ$^9$ desaturase products from TTA were recovered in lipids from heart and gills.

The percentage of n-3 FAs in the liver, gills and heart also depended on the diet given to the fish. The percentage of EPA+DHA was significantly higher in fish fed the 1.5% TTA diet than in control fish, in all the lipid fractions of the gills and heart. In the liver, on the other hand, TTA led to only a moderate increase in the percentage of DHA and a slightly reduced percentage of EPA. The percentage of palmitic acid (16:0) and the sum of all saturated FAs were significantly lower in the PL fraction of the gills, heart and liver of fish fed the 1.5% TTA diet than they were in fish fed the control diet (Tables 7, 8, 9). The sum of monouusaturated FA was significant lower in the TG and FFA factions of gills in fish fed the 1.5% TTA diet than in fish fed the control diet (Table 8). In contrast, the percentage of the sum of monounsaturated FAs in PL and TAG fractions of the liver was higher in fish fed increasing doses of TTA (Table 9).

TABLE 7

Fatty acid composition of the gills

| Fatty acids | Phospholipids | | | Triacylglycerol | | |
|---|---|---|---|---|---|---|
| | FO | 0.5% TTA | 1.5% TTA | FO | 0.5% TTA | 1.5% TTA |
| 14:0 | 3.1 ± 0.17 | 2.9 ± 0.15 | 2.6 ± 0.05 | 5.8 ± 0.09 | 5.6 ± 0.35 | 5.7 ± 0.18 |
| 16:0 | 25.2 ± 0.89$^b$ | 21.7 ± 0.61$^a$ | 20.9 ± 0.09$^a$ | 15 ± 0.24 | 15.3 ± 0.04 | 15.4 ± 0.17 |
| 16:1n − 7 | 2.8 ± 0.14 | 2.8 ± 0.61 | 2.9 ± 0.02 | 6.8 ± 0.44 | 6.1 ± 0.27 | 6.2 ± 0.19 |
| 16:3n − 4 | 0.9 ± 0.22 | 0.8 ± 0.03 | 0.8 ± 0.08 | nd | nd | nd |
| 18:0 | 5.9 ± 0.41 | 5.1 ± 0.31 | 5.1 ± 0.18 | 2.9 ± 0.15 | 2.9 ± 0.12 | 3 ± 0.08 |
| 18:1n − 6 | 0.3 ± 0.07 | 0.4 ± 0.02 | 0.4 ± 0.01 | 0.4 ± 0.01 | 0.4 ± 0.01 | 0.4 ± 0.01 |
| 18:1n − 7 | 3.0 ± 0.07 | 3.2 ± 0.15 | 3.4 ± 0.21 | 3.6 ± 0.05 | 3.6 ± 0.04 | 3.6 ± 0.01 |
| 18:1n − 9 | 14.0 ± 1.42 | 12.6 ± 0.47 | 12.7 ± 0.15 | 15.5 ± 0.45 | 15.7 ± 0.67 | 14.7 ± 0.22 |
| 18:2n − 6 | 1.4 ± 0.75 | 1.01 ± 0.07 | 0.8 ± 0.18 | 2.5 ± 0.07 | 2.6 ± 0.15 | 2.4 ± 0.07 |
| 18:3n − 3 | 0.2 ± 0.19 | 0.1 ± 0.03 | nd | 0.6 ± 0.02 | 0.6 ± 0.05 | 0.5 ± 0.02 |
| 18:3n − 6 | 0.1 ± 0.05 | 0.1 ± 0.06 | nd | nd$^a$ | 1.1 ± 0.08$^b$ | 1.4 ± 0.13$^b$ |
| 18:4n − 3 | nd | nd | nd | 1.2 ± 0.06 | nd | 0.4 ± 0.38 |
| TTA | nd | nd | 0.8 ± 0.17 | nd | nd | 0.7 ± 0.37 |
| 20:1n − 9 | 0.3 ± 0.07 | 0.2 ± 0.01 | 0.3 ± 0.09 | 0.5 ± 0.03 | 0.5 ± 0.02 | 0.5 ± 0.04 |
| 20:1n − 11 | 3.5 ± 0.11 | 3.8 ± 0.43 | 3.5 ± 0.18 | 14.7 ± 0.64 | 15.0 ± 0.80 | 13.6 ± 0.58 |
| 20:2n − 6 | nd | nd | nd | 0.2 ± 0.11 | 0.2 ± 0.10 | 0.1 ± 0.10 |
| 20:3n − 6 | nd | 0.1 ± 0.01 | nd | nd | nd | 0.1 ± 0.07 |
| 20:4n − 3 | 0.27 ± 0.08 | 0.2 ± 0.002 | 0.3 ± 0.07 | 0.7 ± 0.02 | 0.6 ± 0.03 | 0.7 ± 0.01 |
| 20:4n − 6 | 2.5 ± 0.10 | 2.5 ± 0.12 | 2.9 ± 0.21 | 0.6 ± 0.05 | 0.5 ± 0.05 | 0.7 ± 0.12 |
| 20:5n − 3 | 6.2 ± 0.52 | 6.5 ± 0.23 | 6.9 ± 0.62 | 3.9 ± 0.25$^{ab}$ | 3.5 ± 0.10$^a$ | 4 ± 0.09$^b$ |
| 22:1n − 9 | nd | nd | nd | nd | nd | nd |
| 22:1n − 11 | 0.8 ± 0.41 | 1.4 ± 0.44 | 1.03 ± 0.02 | 10.4 ± 0.30$^{ab}$ | 11.7 ± 0.51$^b$ | 10.1 ± 0.50$^a$ |
| 22:5n − 3 | 0.8 ± 0.17 | 1.1 ± 0.003 | 1.2 ± 0.09 | 1.2 ± 0.05 | 1.0 ± 0.01 | 1.2 ± 0.02 |
| 22:6n − 3 | 22.0 ± 1.27$^a$ | 24.7 ± 0.71$^a$ | 27.8 ± 0.57$^b$ | 9.3 ± 0.52 | 9.2 ± 0.54 | 11.6 ± 0.42 |
| Others$^\square$ | 1.9 ± 0.29 | 5.0 ± 1.72 | 2.9 ± 0.34 | 1.5 ± 0.56 | 0.7 ± 0.09 | 0.8 ± 0.12 |
| Σsaturated | 36.2 ± 1.03$^b$ | 30.9 ± 0.62$^a$ | 29.1 ± 0.32$^a$ | 24.0 ± 0.40 | 24.1 ± 0.19 | 24.3 ± 0.13 |
| ΣMonounsaturated | 25.8 ± 1.97 | 25.5 ± 2.04 | 25.6 ± 0.53 | 52.1 ± 0.92$^{ab}$ | 53.1 ± 0.93$^b$ | 49.1 ± 1.12$^a$ |
| Σn − 6 | 4.3 ± 1.10 | 3.7 ± 0.07 | 3.9 ± 0.18 | 3.4 ± 0.14 | 4.5 ± 0.07 | 4.6 ± 0.11 |
| Σn − 3 | 29.7 ± 1.45$^a$ | 33.0 ± 0.86$^a$ | 36.9 ± 0.95$^b$ | 16.8 ± 0.87$^{ab}$ | 14.9 ± 0.44$^a$ | 18.4 ± 0.58$^b$ |

| Fatty acids | Free fatty acids | | |
|---|---|---|---|
| | FO | 0.5% TTA | 1.5% TTA |
| 14:0 | 2.5 ± 0.04$^b$ | 2.4 ± 0.14$^b$ | 2.0 ± 0.08$^a$ |
| 16:0 | 20.4 ± 0.12$^c$ | 17.8 ± 0.38$^b$ | 15.7 ± 0.43$^a$ |
| 16:1n − 7 | 4.1 ± 0.02$^b$ | 4.0 ± 0.24$^b$ | 3.5 ± 0.12$^a$ |
| 16:3n − 4 | 1.0 ± 0.05 | 0.9 ± 0.024 | 0.9 ± 0.05 |
| 18:0 | 5.6 ± 0.07 | 5.1 ± 0.04 | 5.1 ± 0.62 |
| 18:1n − 6 | 0.5 ± 0.02 | 0.4 ± 0.01 | 0.4 ± 0.003 |
| 18:1n − 7 | 4.3 ± 0.12$^b$ | 4.0 ± 0.05$^{ab}$ | 3.8 ± 0.15$^a$ |
| 18:1n − 9 | 15.6 ± 0.47 | 14.7 ± 0.47 | 14.2 ± 0.36 |
| 18:2n − 6 | 1.6 ± 0.01 | 1.7 ± 0.08 | 1.4 ± 0.07 |
| 18:3n − 3 | 0.2 ± 0.01 | 0.2 ± 0.03 | 0.2 ± 0.01 |
| 18:3n − 6 | nd | nd | nd |
| 18:4n − 3 | 0.3 ± 0.01$^b$ | 0.1 ± 0.7$^{ab}$ | 0.2 ± 0.03$^{ab}$ |
| TTA | nd | nd | 0.7 ± 0.36 |
| 20:1n − 9 | 4.5 ± 0.20$^b$ | 3.8 ± 0.08$^a$ | 3.4 ± 0.07$^a$ |
| 20:1n − 11 | 0.5 ± 0.01$^a$ | 0.4 ± 0.02$^b$ | 0.4 ± 0.04$^b$ |
| 20:2n − 6 | 0.3 ± 0.004 | 0.3 ± 0.02 | 0.3 ± 0.03 |
| 20:3n − 6 | 0.3 ± 0.01 | 0.3 ± 0.01 | 0.3 ± 0.02 |
| 20:4n − 3 | 0.4 ± 0.07 | 0.5 ± 0.02 | 0.5 ± 0.02 |
| 20:4n − 6 | 5.6 ± 0.26$^a$ | 6.0 ± 0.08$^{ab}$ | 6.2 ± 0.33$^{ab}$ |
| 20:5n − 3 | 9.2 ± 0.30 | 10.1 ± 0.23 | 10.1 ± 0.53 |
| 22:1n − 9 | 0.2 ± 0.02$^b$ | nd$^a$ | nd$^{da}$ |
| 22:1n − 11 | 1.2 ± 0.12$^b$ | 0.8 ± 0.15$^{ab}$ | 0.6 ± 0.08$^a$ |
| 22:5n − 3 | 1.6 ± 0.04$^a$ | 2.0 ± 0.14$^{ab}$ | 2.3 ± 0.19$^b$ |
| 22:6n − 3 | 17.2 ± 0.09$^a$ | 21.8 ± 1.5$^b$ | 23.9 ± 0.67$^b$ |
| Others$^\square$ | 2.0 ± 0.17 | 2.0 ± 0.36 | 4.6 ± 1.01 |
| Σsaturated | 29.0 ± 0.13$^b$ | 25.7 ± 0.54$^a$ | 23.3 ± 1.30$^a$ |
| ΣMonounsaturated | 31.2 ± 0.83$^b$ | 28.4 ± 0.99$^a$ | 25.6 ± 0.64$^a$ |
| Σn − 6 | 8.2 ± 0.26 | 8.6 ± 0.12 | 8.6 ± 0.37 |
| Σn − 3 | 28.6 ± 0.38$^a$ | 34.3 ± 1.58$^b$ | 36.6 ± 1.23$^b$ |

FO: fish oil, 0.5% TTA: fish oil added 0.5% TTA, 1.5% TTA: fish oil added 1.5% TTA. The quantity of each fatty acid is given as percentage of the total fatty acids (FA). Data are means ± SEM. Values within the same row with different superscripts are significantly different, $p < 0.05$, n = 3; nd = not detected.
$^\square$Includes nd, FA, and some FA with percentages less than 1.

TABLE 8

Fatty acid composition of the heart.

| Fatty acids | Phospholipids | | | Triacylglycerol | | |
|---|---|---|---|---|---|---|
| | FO | 0.5% TTA | 1.5% TTA | FO | 0.5% TTA | 1.5% TTA |
| 14:0 | 1.6 ± 0.20 | 1.6 ± 0.16 | 1.2 ± 0.22 | 6.2 ± 0.35 | 6.1 ± 0.20 | 5.9 ± 0.20 |
| 16:0 | 22.8 ± 0.12$^b$ | 22.2 ± 0.5$^b$ | 19.0 ± 0.79$^a$ | 14.4 ± 1.2 | 13.9 ± 0.70 | 13.8 ± 0.19 |
| 16:1n − 7 | 1.6 ± 0.01 | 1.8 ± 0.17 | 1.8 ± 0.09 | 6.7 ± 0.18 | 6.7 ± 0.34 | 6.6 ± 0.07 |
| 18:0 | 4.1 ± 0.19 | 3.9 ± 0.09 | 3.5 ± 0.22 | 2.3 ± 0.15 | 2.2 ± 0.07 | 2.3 ± 0.14 |
| 18:1n − 6 | 0.3 ± 0.05 | 0.3 ± 0.05 | 0.3 ± 0.01 | 0.3 ± 0.13 | 0.4 ± 0.01 | 0.4 ± 0.01 |
| 18:1n − 7 | 2.7 ± 0.15 | 2.9 ± 0.06 | 3.0 ± 0.1 | 3.8 ± 0.09 | 3.6 ± 0.11 | 3.6 ± 0.09 |
| 18:1n − 9 | 7.2 ± 0.09 | 8.3 ± 0.20 | 8.0 ± 0.19 | 15.0 ± 0.14 | 14.5 ± 0.15 | 14.1 ± 0.22 |
| 18:2n − 6 | 1.0 ± 0.20 | 1.0 ± 0.09 | 1.2 ± 0.05 | 2.4 ± 0.22 | 2.1 ± 0.46 | 2.5 ± 0.07 |
| 18:3n − 3 | nd | nd | 0.1 ± 0.08 | 0.4 ± 0.19 | 0.9 ± 0.33 | 0.6 ± 0.01 |
| 18:4n − 3 | nd$^a$ | nd$^{ab}$ | 0.2 ± 0.01$^b$ | nd | nd | nd |
| TTA | | nd | 0.7 ± 0.4 | | nd | nd |
| 20:1n − 9 | 3.8 ± 0.07$^a$ | 4.3 ± 0.29$^{ab}$ | 4.5 ± 0.13$^b$ | 16.9 ± 0.69 | 16.2 ± 0.56 | 16.6 ± 0.81 |
| 20:1n − 11 | nd | nd | nd | 0.4 ± 0.19 | 0.5 ± 0.04 | 0.5 ± 0.03 |
| 20:2n − 6 | nd | nd | 0.2 ± 0.003 | 0.2 ± 0.11 | 0.2 ± 0.1 | 0.3 ± 0.01 |
| 20:3n − 6 | nd | nd | 0.1 ± 0.07 | nd$^a$ | 0.1 ± 0.03$^b$ | nd$^a$ |
| 20:4n − 3 | 0.8 ± 0.04 | 0.5 ± 0.07 | 0.7 ± 0.09 | 0.5 ± 0.27 | 0.7 ± 0.01 | 0.7 ± 0.052 |
| 20:4n − 6 | 1.5 ± 0.03 | 1.4 ± 0.07 | 1.5 ± 0.08 | 0.1 ± 0.06 | nd | 0.2 ± 0.08 |
| 20:5n − 3 | 10.7 ± 0.27$^b$ | 9.0 ± 0.51$^b$ | 8.4 ± 0.09$^a$ | 3.3 ± 0.05$^a$ | 3.4 ± 0.06$^a$ | 3.7 ± 0.05$^b$ |
| 22:1n − 9 | 0.8 ± 0.09 | 1.0 ± 0.15 | 1.0 ± 0.09 | 1.2 ± 0.59 | 1.7 ± 0.02 | 1.7 ± 0.08 |
| 22:1n − 11 | nd | nd | nd | 11.23 ± 0.24 | 11.6 ± 0.27 | 11.4 ± 0.32 |
| 22:5n − 3 | 1.8 ± 0.06$^a$ | 2.0 ± 0.05$^a$ | 2.4 ± 0.06$^b$ | 0.8 ± 0.38 | 1.1 ± 0.06 | 1.2 ± 0.06 |
| 22:6n − 3 | 35.5 ± 0.08 | 35.9 ± 1.39 | 38.5 ± 1.4 | 7.9 ± 0.44 | 7.6 ± 0.37 | 8.4 ± 0.43 |
| others$^\Box$ | 1.4 ± 0.21 | 1.3 ± 0.22 | 1.8 ± 0.03 | 0.2 ± 0.09 | 0.4 ± 0.06 | 0.4 ± 0.10 |
| ΣSaturated | 32.2 ± 3.09$^b$ | 28.1 ± 0.76$^b$ | 24.3 ± 1.00$^a$ | 24.8 ± 2.57 | 22.8 ± 0.89 | 23.0 ± 0.42 |
| ΣMonounsaturated | 12.7. ± 3.02 | 17.8 ± 0.59 | 17.8 ± 0.76 | 55.6 ± 1.54 | 55.3 ± 1.22 | 55.5 ± 1.40 |
| Σn − 6 | 2.3 ± 0.25 | 2.6 ± 0.17 | 3.0 ± 0.15 | 2.7 ± 0.34 | 2.4 ± 0.41 | 2.8 ± 0.07 |
| Σn − 3 | 49.5 ± 0.60 | 47.5 ± 1.6 | 50.4 ± 1.4 | 13.7 ± 1.42 | 15.2 ± 0.83 | 16.1 ± 0.74 |

| Fatty acids | Free fatty acids | | |
|---|---|---|---|
| | FO | 0.5% TTA | 1.5% TTA |
| 14:0 | 1.2 ± 0.14 | 1.5 ± 0.09 | 1.5 ± 0.14 |
| 16:0 | 21.9 ± 0.93 | 21.1 ± 0.59 | 20.4 ± 1.16 |
| 16:1n − 7 | 2.0 ± 0.11 | 1.4 ± 0.7 | 2.1 ± 0.1 |
| 18:0 | 5.2 ± 0.4$^b$ | 5.0 ± 0.26$^{ab}$ | 4.2 ± 0.20$^a$ |
| 18:1n − 6 | nd$^a$ | 0.4 ± 0.01$^b$ | 0.3 ± 0.01$^b$ |
| 18:1n − 7 | 3.6 ± 0.09 | 3.5 ± 0.20 | 3.3 ± 0.15 |
| 18:1n − 9 | 8.4 ± 0.10 | 8.6 ± 0.40 | 8.2 ± 0.47 |
| 18:2n − 6 | 1.5 ± 0.14 | 1.4 ± 0.07 | 1.1 ± 0.14 |
| 18:3n − 3 | nd | 0.2 ± 0.08 | nd |
| 18:4n − 3 | nd | nd | nd |
| TTA | nd | nd | nd |
| 20:1n − 9 | 5.9 ± 0.15$^b$ | 5.9 ± 0.18$^b$ | 5.2 ± 0.13$^a$ |
| 20:1n − 11 | nd | nd | nd |
| 20:2n − 6 | nd | nd | nd |
| 20:3n − 6 | nd | nd | nd |
| 20:4n − 3 | 0.5 ± 0.26 | 0.7 ± 0.14 | 0.6 ± 0.07 |
| 20:4n − 6 | | | |
| 20:5n − 3 | 9.8 ± 0.65 | 8.9 ± 0.50 | 9.3 ± 0.42 |
| 22:1n − 9 | nd | nd | nd |
| 22:1n − 11 | 2.1 ± 0.17$^b$ | 2.1 ± 0.13$^b$ | 1.4 ± 0.16$^a$ |
| 22:5n − 3 | 1.8 ± 0.07$^a$ | 2.0 ± 0.05$^b$ | 2.3 ± 0.03$^c$ |
| 22:6n − 3 | 30.7 ± 0.82$^a$ | 33.2 ± 1.07$^a$ | 35.3 ± 1.5$^b$ |
| others$^\Box$ | 1.3 ± 0.60 | 1.4 ± 0.45 | 1.4 ± 0.91 |
| ΣSaturated | 28.4 ± 0.83 | 27.7 ± 0.97 | 26.4 ± 1.19 |
| ΣMonounsaturated | 22.3 ± 0.47 | 21.9 ± 0.97 | 20.7 ± 0.87 |
| Σn − 6 | 3.2 ± 0.21 | 3.5 ± 0.08 | 3.2 ± 0.08 |
| Σn − 3 | 42.9 ± 0.5 | 45.0 ± 1.71 | 47.5 ± 1.36 |

FO: fish oil, 0.5% TTA: fish oil added 0.5% TTA, 1.5% TTA: fish oil added 1.5% TTA. The quantity of each fatty acid is given as percentage of the total fatty acids (FA). Data are means ± SEM. Values within the same row with different superscripts are significantly different, $p < 0.05$, n = 3; nd = not detected.
$^\Box$Includes nd. FAs and some FAs with percentages less than 1.

TABLE 9

Fatty acid composition of the liver.

| Fatty acids | Phospholipids | | | Triacylglycerol | | |
|---|---|---|---|---|---|---|
| | FO | 0.5% TTA | 1.5% TTA | FO | 0.5% TTA | 1.5% TTA |
| 14:0 | 2.6 ± 0.06[b] | 2.3 ± 0.09[a] | 2.2 ± 0.05[a] | 3.5 ± 0.65 | 3.8 ± 0.36 | 2.6 ± 1.16 |
| 16:0 | 21.3 ± 0.90[b] | 17.3 ± 0.36[a] | 17.2 ± 0.41[a] | 10.0 ± 0.58 | 9.7 ± 1.62 | 6.7 ± 3.34 |
| 16:1n − 7 | 1.7 ± 0.04[b] | 1.7 ± 0.02[ab] | 1.6 ± 0.03[a] | 6.1 ± 0.06 | 5.6 ± 0.05 | 4.8 ± 0.8 |
| 16:3n − 4 | 0.5 ± 0.05 | 0.5 ± 0.02 | 0.5 ± 0.04 | 0.4 ± 0.03 | 0.4 ± 0.06 | 0.2 ± 0.11 |
| 18:0 | 2.9 ± 0.3[a] | 3.6 ± 0.17[b] | 3.5 ± 0.04[b] | 2.5 ± 0.39 | 2.1 | 2.5 ± 0.19 |
| 18:1n − 6 | 0.4 ± 0.01[a] | 0.4 ± 0.02[b] | 0.4 ± 0.01[ab] | 0.4 ± 0.004 | 0.3 ± 0.001 | nd |
| 18:1n − 7 | 1.9 ± 0.08[a] | 2.3 ± 0.09[b] | 2.1 ± 0.04[ab] | 4.5 ± 0.21 | 4.6 ± 0.61 | 4.4 ± 0.19 |
| 18:1n − 9 | 8.6 ± 0.19 | 9.3 ± 0.18 | 9.3 ± 0.27 | 25.2 ± 2.14 | 23.5 ± 2.8 | 25.4 ± 4.60 |
| 18:2n − 6 | 1.1 ± 0.11 | 1.5 ± 0.12 | 1.4 ± 0.02 | 2.3 ± 0.22 | 2.7 ± 0.13 | 3.2 ± 0.87 |
| 18:3n − 3 | nd | nd | nd | 0.4 ± 0.08 | 0.5 ± 0.09 | 0.6 ± 0.23 |
| 18:3n − 6 | nd | 0.1 ± 0.004 | 0.1 ± 0.004 | nd | nd | nd |
| 18:4n − 3 | nd[a] | 0.1 ± 0.03[b] | 0.1 ± 0.00[b] | 0.7 ± 0.10 | 0.8 ± 0.18 | 0.5 ± 0.27 |
| $\Delta^9$-desaturased TTA | | 0.1 ± 0.01 | 0.1 ± 0.01 | | nd | nd |
| TTA | | 0.05 ± 0.02 | nd | | nd | nd |
| 20:1n − 9 | 0.1 ± 0.07[a] | 0.2 ± 0.01[b] | 0.2 ± 0.01[b] | 0.5 ± 0.01 | 0.3 ± 0.01 | 0.5 ± 0.001 |
| 20:1n − 11 | 4.6 ± 0.24[a] | 5.2 ± 0.25[b] | 5.2 ± 0.05[a] | 17.3 ± 0.89 | 16.7 ± 0.65 | 16.6 ± 0.28 |
| 20:2n − 6 | 0.4 ± 0.03 | 0.4 ± 0.02 | 0.4 ± 0.01 | 0.4 ± 0.01 | 0.5 ± 0.07 | 0.4 ± 0.26 |
| 20:3n − 6 | 0.4 ± 0.02 | 0.4 ± 0.02 | 0.4 ± 0.02 | nd | nd | nd |
| 20:4n − 3 | 0.7 ± 0.05 | 0.8 ± 0.02 | 0.8 ± 0.02 | 0.7 ± 0.06 | 0.8 ± 0.08 | 0.4 ± 0.21 |
| 20:4n − 6 | 1.8 ± 0.16[ab] | 1.6 ± 0.06[a] | 2.0 ± 0.06[b] | nd | nd | nd |
| 20:5n − 3 | 10.3 ± 0.78 | 9.7 ± 0.17 | 9.3 ± 0.30 | 2.5 ± 0.13 | 2.7 ± 0.19 | 1.9 ± 0.27 |
| 22:1n − 9 | nd | nd | nd | 1.3 ± 0.03 | 1.3 ± 0.19 | 0.9 ± 0.43 |
| 22:1n − 11 | 0.5 ± 0.09 | 0.4 ± 0.20 | 0.6 ± 0.02 | 8.2 ± 0.53 | 8.7 ± 1.45 | 8.7 ± 0.95 |
| 22:5n − 3 | 1.6 ± 0.81 | 2.6 ± 0.08 | 2.6 ± 0.11 | 1.1 ± 0.004 | 1.3 ± 0.03 | 0.7 ± 0.35 |
| 22:6n − 3 | 35.6 ± 0.51 | 36.2 ± 0.28 | 36.7 ± 0.49 | 5.2 ± 0.49 | 7.3 ± 1.28 | 6.3 ± 0.65 |
| others[□] | 0.7 ± 0.16 | 1.5 ± 0.23 | 1.3 ± 0.06 | 2.9 ± 1.06 | 1.4 ± 0.87 | 4.5 ± 3.08 |
| Σsaturated | 27.5 ± 0.49[b] | 23.8 ± 0.49[a] | 23.6 ± 0.40[a] | 18.4 ± 0.57 | 18.9 ± 1.93 | 20.5 ± 3.66 |
| ΣMonounsaturated | 18.1 ± 0.29[a] | 19.7 ± 0.26[b] | 19.7 ± 0.33[b] | 63.6 ± 2.70[a] | 61.3 ± 2.25[a] | 58.7 ± 0.79[b] |
| Σn − 6 | 3.7 ± 0.38 | 4.1 ± 0.10 | 4.3 ± 0.10 | 2.8 ± 0.34 | 3.1 ± 0.05 | 2.5 ± 0.004 |
| Σn − 3 | 49.9 ± 1.03 | 51.3 ± 0.18 | 51.4 ± 0.14 | 11.7 ± 0.56 | 14.4 ± 1.06 | 12.8 ± 0.20 |

| Fatty acids | Free fatty acids | | |
|---|---|---|---|
| | FO | 0.5% TTA | 1.5% TTA |
| 14:0 | 3.9 ± 0.57 | 4.0 ± 0.04 | 3.5 ± 0.16 |
| 16:0 | 17.7 ± 1.7 | 16.6 ± 0.58 | 16.1 ± 0.35 |
| 16:1n − 7 | 5.0 ± 0.93 | 5.0 ± 0.13 | 5.0 ± 0.09 |
| 16:3n − 4 | 0.8 ± 0.07 | 0.9 ± 0.01 | 0.8 ± 0.06 |
| 18:0 | 2.8 ± 0.14 | 2.2 ± 0.31 | 2.4 ± 0.08 |
| 18:1n − 6 | 0.5 ± 0.07 | 0.5 ± 0.002 | 0.5 ± 0.03 |
| 18:1n − 7 | 3.9 ± 0.13 | 4.4 ± 0.09 | 4.4 ± 0.15 |
| 18:1n − 9 | 24.9 ± 3.60 | 21.7 ± 0.67 | 23.0 ± 0.72 |
| 18:2n − 6 | 4.0 ± 1.7 | 2.3 ± 0.11 | 2.2 ± 0.14 |
| 18:3n − 3 | 1.0 ± 0.63 | 0.4 ± 0.05 | 0.4 ± 0.05 |
| 18:3n − 6 | nd[a] | 0.1 ± 0.06[b] | nd[a] |
| 18:4n − 3 | 0.4 ± 0.12 | 0.3 ± 0.08 | 0.4 ± 0.09 |
| $\Delta^9$-desaturased TTA | | nd | nd |
| TTA | | nd | nd |
| 20:1n − 9 | 0.3 ± 0.02 | 0.3 ± 0.01 | 0.2 ± 0.11 |
| 20:1n − 11 | 6.7 ± 0.70[a] | 7.8 ± 0.30[ab] | 9.2 ± 0.54[b] |
| 20:2n − 6 | 0.6 ± 0.25 | 0.4 ± 0.01 | 0.4 ± 0.02 |
| 20:3n − 6 | 0.3 ± 0.12[b] | 0.2 ± 0.01[ab] | nd[a] |
| 20:4n − 3 | 1.0 ± 0.10 | 1.2 ± 0.04 | 1.3 ± 0.08 |
| 20:4n − 6 | 0.8 ± 0.07 | 0.8 ± 0.04 | 0.7 ± 0.02 |
| 20:5n − 3 | 5.9 ± 0.77 | 5.9 ± 0.46 | 5.4 ± 0.43 |
| 22:1n − 9 | 0.5 ± 0.07 | 0.6 ± 0.05 | 0.4 ± 0.21 |
| 22:1n − 11 | 1.9 ± 0.3 | 2.5 ± 0.28 | 2.4 ± 0.36 |
| 22:5n − 3 | 1.5 ± 0.23 | 1.7 ± 0.10 | 1.1 ± 0.54 |
| 22:6n − 3 | 11.3 ± 0.69 | 15.1 ± 0.74 | 14.9 ± 0.40 |
| others[□] | 2.4 ± 0.57[a] | 3.0 ± 0.11[ab] | 3.2 ± 0.16[b] |
| Σsaturated | 25.8 ± 2.10 | 24.2 ± 0.75 | 23.4 ± 0.43 |
| ΣMonounsaturated | 43.8 ± 1.65 | 43.0 ± 1.39 | 45.3 ± 1.55 |
| Σn − 6 | 5.8 ± 2.08 | 3.8 ± 0.11 | 3.4 ± 0.13 |
| Σn − 3 | 21.7 ± 1.09 | 25.2 ± 1.27 | 23.9 ± 1.05 |

FO: fish oil, 0.5% TTA: fish oil added 0.5% TTA, 1.5% TTA: fish oil added 1.5% TTA. The quantity of each fatty acid is given as percentage of the total fatty acids (FA). Data are means ± SEM. Values within the same row with different superscripts are significantly different, $p < 0.05$, n = 3; nd = not detected.
[□]Includes nd. FAs and some FAs with percentages less than 1.

2.4 Biological Effects of the Composition According to the Invention Including a Fermented Soy Protein Material Chemicals Gendaxin was obtained from Aximed, Bergen, Norway. One capsule of Gendaxin® contains 35 mg isoflavones, inter alia 10 mg Genistein and 15 mg Daidzein.

Lipid Analysis

Plasma lipids were measured enzymatically on the Technicon Axon system (Miles, Tarrytown, N.Y.) using the Triglyceride kit from Bayer, Total cholesterol (Bayer, Tarrytown, N.Y.), and the PAP150 kit for choline containing phospholipids from bioMerieux. The results were given in mmol/l, and the data is presented in table 10 below.

TABLE 10

Total cholesterol, triglycerides and phospholipids of the plasma.

| | Cholesterol | Triglycerides | Phospholipids |
|---|---|---|---|
| Control | 10.02 | 2.95 | 11.98 |
| 0.25% Gendaxin | 9.14 | 2.71 | 11.19 |
| 0.5% Gendaxin + 0.9% TTA | 9.10 | 2.12 | 10.66 |

It is evident from the above data that addition of Gendaxin to the fish feed has a positive effect on the fatty acid composition of the plasma of the salmon. The cholesterol, triglyceride and phospholipids levels all decreased with 0.25% Gendaxin added to te fish feed when compared to the control. Further addition of Gendaxin and TTA improved the fatty acid composition of the plasma additionally.

Enzyme Assay

Fatty acyl-CoA oxidase activity was measured in the peroxisomal liver fraction as previously described (Small G M, Burdett K, Connock M S (1985) Biochem J 227: 205-10). The results were given as fatty acyl-CoA oxidase activity per total protein, and are shown in table 11 below.

TABLE 11

Hepatic β-oxidation.

| | Beta oxidation |
|---|---|
| Control | 0.940 |
| 0.5% Gendaxin + 0.9% TTA | 1.501 |

It is evident from the above data that addition of Gendaxin and TTA to the fish feed has a positive effect on β-oxidation, as the β-oxidation is highly increased.

EXAMPLE 3

In line with the experimental setup given in example 1, we have conducted a feeding experiment on Male Wistar rats (see Table 12) with the following feed components:

30% fat
20% protein
5% fiber
10% sucrose
3.5% AIN93G mineral mix
1.0% AIN-93 vitamin mix
The remaining: Starch The fat component is 30% lard, or 2.5-5% of the lard is exchanged with fish oil or 0.15 of the lard is exchanged with TTA. The protein material is 20% milk protein (casein), or half of it is exchanged with fish protein or "Bioprotein".

TABLE 12

| Treatment | Ch mmol/L | Tg mmol/L | HDL Ch mmol/L | FFA mmol/L | PL mmol/L | HDL Ch/Ch ratio |
|---|---|---|---|---|---|---|
| FPH, 10% | 2.03 | 1.16 | 1.63 | 0.34 | 1.48 | 0.80 |
| Fish oil, 2.5% | 1.77 | 1.27 | 1.42 | 0.40 | 1.47 | 0.80 |
| Fish oil, 5% | 1.79 | 1.13 | 1.44 | 0.40 | 1.41 | 0.81 |
| Fish oil 2.5% + FPH 10% | 1.26 | 0.93 | 1.00 | 0.35 | 1.07 | 0.79 |
| Fish oil 5% + FPH 10% | 1.21 | 0.92 | 0.97 | 0.37 | 0.98 | 0.80 |
| FPH 10% + TTA 0.15% | 1.27 | 0.65 | 1.07 | 0.28 | 1.18 | 0.83 |
| Fish oil 2.5% + TTA 0.15% | 1.21 | 0.43 | 1.00 | 0.25 | 1.01 | 0.83 |
| Fish oil 5% + TTA 0.15% | 1.26 | 0.61 | 1.02 | 0.23 | 1.14 | 0.81 |
| Fish oil 2.5% + FPH 10% + TTA 0.15% | 0.98 | 0.46 | 0.81 | 0.31 | 1.00 | 0.83 |
| Fish oil 5% + FPH 10% + TTA 0.15% | 1.02 | 0.72 | 0.84 | 0.32 | 1.00 | 0.84 |
| TTA 0.15% | 1.56 | 0.39 | 1.31 | 0.28 | 1.17 | 0.84 |
| Bioprotein High 20% | 1.23 | 0.80 | 0.95 | 0.41 | 1.00 | 0.77 |
| Bioprotein Low 20% | 1.28 | 0.61 | 1.04 | 0.34 | 1.01 | 0.81 |
| Kontroll (Casein 20%) | 1.90 | 1.04 | 1.52 | 0.38 | 1.41 | 0.80 |

| | Weight of rat gram | Liver gram | WAT epi gram | WAT ret gram | Liver/bw ratio | WAT epi/bw ratio | WAT ret/bw ratio |
|---|---|---|---|---|---|---|---|
| FPH, 10% | 460.83 | 10.04 | 7.99 | 9.90 | 2.17 | 1.69 | 2.12 |
| Fish oil, 2.5% | 427.83 | 9.44 | 7.00 | 8.67 | 2.21 | 1.63 | 2.01 |
| Fish oil, 5% | 445.17 | 9.87 | 7.59 | 9.79 | 2.21 | 1.70 | 2.20 |
| Fish oil 2.5% + FPH 10% | 438.83 | 10.01 | 6.33 | 8.80 | 2.28 | 1.42 | 2.02 |
| Fish oil 5% + FPH 10% | 432.50 | 10.18 | 7.31 | 8.86 | 2.35 | 1.67 | 2.05 |
| Fish oil 2.5% + FPH 10% + TTA 0.15% | 438.50 | 15.66 | 6.03 | 8.20 | 3.57 | 1.36 | 1.85 |
| Fish oil 5% + FPH 10% + TTA 0.15% | 449.67 | 16.29 | 7.18 | 9.19 | 3.62 | 1.58 | 2.02 |
| TTA 0.15% | 404.67 | 13.13 | 4.25 | 6.28 | 3.26 | 1.05 | 1.55 |
| Bioprotein High 20% | 413.33 | 9.00 | 5.02 | 6.99 | 2.18 | 1.21 | 1.69 |
| Bioprotein Low 20% | 420.67 | 8.97 | 4.63 | 6.65 | 2.13 | 1.09 | 1.58 |
| Kontroll (Casein 20%) | 417.36 | 8.91 | 5.94 | 8.46 | 2.13 | 1.42 | 2.03 |

The invention clamed is:

1. A method of treatment of insulin resistance, obesity, diabetes, fatty liver, hypercholesterolemia, dyslipidemia, atherosclerosis, coronary heart disease, thrombosis, stenosis, secondary stenosis, myocardial infarction, stroke, elevated blood pressure, endothelial dysfunction, procoagulant state, polycystic ovary syndrome, the metabolic syndrome, reducing the growth of cancer cells and/or inhibiting the metastasis of metastatic neoplasms, an inflammatory disorder, and a proliferate skin disorder comprising the administration of a pharmaceutical or nutritional composition comprising a combination of:

1) a protein material; and
2) one or more compounds comprising non β-oxidizable fatty acid entities represented by
   (a) the general formula R''—COO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group; and R'' is a hydrogen atom or an alkyl group containing from 1 to 4 carbon atoms; and/or
   (b) the general formula (I),

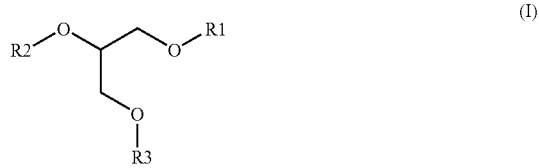

wherein R1, R2, and R3 represent
   i) a hydrogen atom; or
   ii) a group having the formula CO—R in which R is a linear or branched alkyl group, saturated or unsaturated, optionally substituted, and the main chain of said R contains from 1 to 25 carbon atoms; or
   iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
   iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);

wherein R1, R2, and R3 are chosen independently from i), ii), iii), or iv), but at least one of R1, R2, or R3 is defined by iii); and/or (c) the general formula (II),

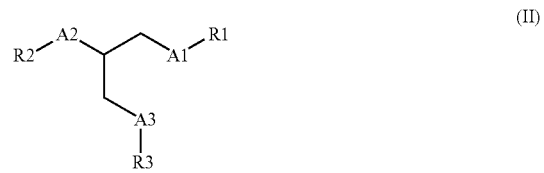

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;

wherein R1, R2, and R3 represent
   i) a hydrogen atom or a linear or branched alkyl group, saturated or unsaturated, optionally substituted, containing from 1 to 23 carbon atoms; or
   ii) a group having the formula CO—R in which R is a linear or branched alkyl group, saturated or unsaturated, optionally substituted, and the main chain of said R contains from 1 to 25 carbon atoms; or
   iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
   iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);

wherein R1, R2, and R3 are chosen independently from i), ii), iii), or iv), but at least one of R1, R2, or R3 is defined by iii); and/or a salt, prodrug or complex of the compounds according to (a)-(c).

2. Method according to claim 1, where said treatment of reducing the growth of cancer cells and/or inhibiting the metastasis of metastatic neoplasms includes inhibition of: primary and secondary neoplasms, the growth of tumours, invasion of a primary tumour into connective tissue and formation of secondary tumours.

3. Method according to claim 1 where the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders, various immune mediated neurological disorders, various cardiovascular disorders, inflammatory bowel diseases and Chron's disease, non specific colitis, pancreatitis, nephritis, cholestatis/fibrosis of the liver, and acute and chronic allograft rejection after organ transplantation, and diseases that have an inflammatory component.

4. Method according to claim 1, where said proliferate skin disorder is selected from the group comprising psoriasis, atopic dermatitis, non-specific dermatitis, primary irritant contact-dermatitis, allergic contact-dermatitis, lamellar ichthyosis, epidermolytic hyperkeratoses, pre-malign sun-induced keratoses, and seborrhoea.

5. A method of improving the total body lipid composition of an animal comprising the administration or feeding of an animal feed comprising common feed components and a combination of:
1) a protein material; and
2) one or more compounds comprising non β-oxidizable fatty acid entities represented by
(a) the general formula R''—COO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group; and R'' is a hydrogen atom or an alkyl group containing from 1 to 4 carbon atoms; and/or
(b) the general formula (I),

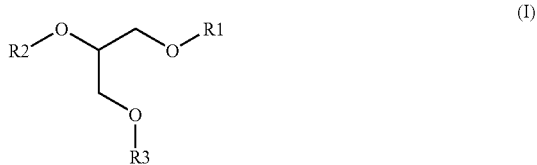

(I)

wherein R1, R2, and R3 represent
i) a hydrogen atom; or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or (c) the general formula (II),

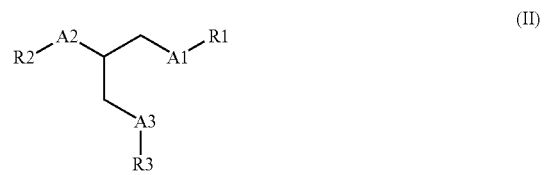

(II)

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;
wherein R1, R2, and R3 represent
i) a hydrogen atom or a linear or branched alkyl group, saturated or unsaturated, optionally substituted, containing from 1 to 23 carbon atoms; or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or
a salt, prodrug or complex of the compounds according to (a)-(c).

6. Method according to claim 5, where the improvement of the total lipid composition comprises decreasing the total body lipid levels.

7. Method according to claim 5, where the improvement of the total lipid composition comprises decreasing the total body saturated fatty acid levels.

8. Method according to claim 5, where the improvement of the total lipid composition comprises increasing the total body n-3 fatty acid levels.

9. Method according to claim 1, wherein said protein material is fermented.

10. Method according to claim 5, wherein said protein material is fermented.

11. Method according to claim 1, wherein said protein material is a single cell protein material (SCP).

12. Method according to claim 5, wherein said protein material is a single cell protein material (SCP).

13. Method according to claim 1, wherein said protein material is a fish protein hydrolysate.

14. Method according to claim 5, wherein said protein material is a fish protein hydrolysate.

15. Method according to claim 1, where said protein material is soy protein.

16. Method according to claim 5, where said protein material is soy protein.

17. Method according to claim 1, wherein said protein material is a fermented soy protein material.

18. Method according to claim 5, wherein said protein material is a fermented soy protein material.

19. Method according to claim 1, wherein said protein material is GENDAXIN® (isoflavone concentrate).

20. Method according to claim 5, wherein said protein material is GENDAXIN® (isoflavone concentrate).

21. Method according to claim 1, where the compound(s) comprising a non β-oxidizable fatty acid entity are non β-oxidizable fatty acids.

22. Method according to claim 5, where the compound(s) comprising a non β-oxidizable fatty acid entity are non β-oxidizable fatty acids.

23. Method according to claim 1, where the compound(s) comprising a non β-oxidizable fatty acid entity are tetradecylthioacetic acid (TTA), tetradecylselenoacetic acid and/or 3-Thia-15-heptadecyne.

24. Method according to claim 5, where the compound(s) comprising a non β-oxidizable fatty acid entity are tetradecylthioacetic acid (TTA), tetradecylselenoacetic acid and/or 3-Thia-15-heptadecyne.

25. Method according to claim 1, where X is a sulphur atom or a selenium atom.

26. Method according to claim 5, where X is a sulphur atom or a selenium atom.

27. Method according to claim 1, where the compound(s) comprising a non β-oxidizable fatty acid entity is a phospholipid, wherein said phospholipid is selected from the group comprising phosphatidyl serine, phosphatidyl choline, phosphatidyl ethanolamine, phosphatidyl inositol, phosphatidyl glycerol, and/or diphosphatidyl glycerol.

28. Method according to claim 5, where the compound(s) comprising a non β-oxidizable fatty acid entity is a phospholipid, wherein said phospholipid is selected from the group comprising phosphatidyl serine, phosphatidyl choline, phosphatidyl ethanolamine, phosphatidyl inositol, phosphatidyl glycerol, and/or diphosphatidyl glycerol.

29. Method according to claim 1, where the compound comprising a non β-oxidizable fatty acid entity is the phosphatidyl choline derivative 1,2-ditetradecylthioacetoyl-sn-glycero-3-phosphocholine.

30. Method according to claim 5, where the compound comprising a non β-oxidizable fatty acid entity is the phosphatidyl choline derivative 1,2-ditetradecylthioacetoyl-sn-glycero-3-phosphocholine.

31. Method according to claim 1, where the compound comprising a non β-oxidizable fatty acid entity is the phosphatidyl ethanolamine derivative 1,2-ditetradecylthioacetoyl-sn-glycero-3-phosphoethanolamine.

32. Method according to claim 5, where the compound comprising a non β-oxidizable fatty acid entity is the phosphatidyl ethanolamine derivative 1,2-ditetradecylthioacetoyl-sn-glycero-3-phosphoethanolamine.

33. Method according to claim 1, where the compound(s) comprising a non β-oxidizable fatty acid entity are mono-, di- or tri-acylglycerides.

34. Method according to claim 5, where the compound(s) comprising a non β-oxidizable fatty acid entity are mono-, di- or tri-acylglycerides.

35. Method according to claim 1, where the compound(s) comprising a non β-oxidizable fatty acid entity are tri-acylglycerides comprising tetradecylthioacetic acid (TTA).

36. Method according to claim 5, where the compound(s) comprising a non β-oxidizable fatty acid entity are tri-acylglycerides comprising tetradecylthioacetic acid (TTA).

37. Method according to claim 1, wherein the composition or animal feed further comprises a plant and/or fish oil.

38. Method according to claim 5, wherein the composition or animal feed further comprises a plant and/or fish oil.

39. A method of treatment of hypercholesterolemia and conditions negatively effected by high cholesterol levels, insulin resistance, obesity, diabetes, fatty liver, dyslipidemia, atherosclerosis, coronary heart disease, thrombosis, stenosis, secondary stenosis, myocardial infarction, stroke, elevated blood pressure, endothelial dysfunction, procoagulant state, polycystic ovary syndrome, the metabolic syndrome, reducing the growth of cancer cells and/or inhibiting the metastasis of metastatic neoplasms, inflammatory disorders and proliferate skin disorders comprising the administration of a preparation comprising a combination of:
   1) a protein material, and
   2) a plant or fish oil,
   wherein the protein material is chosen from the group comprising single cell protein material (SCP), fish protein hydrolysate, and a fermented soy protein material.

40. Method according to claim 39, wherein said protein material is GENDAXIN® (isoflavone concentrate).

41. Method according to claim 37, where the plant or fish oil comprise polyunsaturated fatty acids.

42. Method according to claim 38, where the plant or fish oil comprise polyunsaturated fatty acids.

43. Method according to claim 39, where the plant or fish oil comprise polyunsaturated fatty acids.

44. Method according to claim 37, where the plant oil is selected from the group comprising sunflower oil, soy oil and olive oil.

45. Method according to claim 38, where the plant oil is selected from the group comprising sunflower oil, soy oil and olive oil.

46. Method according to claim 39, where the plant oil is selected from the group comprising sunflower oil, soy oil and olive oil.

47. Method according to claim 39, where said treatment of reducing the growth of cancer cells and/or inhibiting the metastasis of metastatic neoplasms includes inhibition of: primary and secondary neoplasms, the growth of tumours, invasion of a primary tumour into connective tissue and formation of secondary tumours.

48. Method according to claim 39, where the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders, various immune mediated neurological disorders, various cardiovascular disorders, inflammatory bowel diseases and Chron's disease, non specific colitis, pancreatitis, nephritis, cholestatis/fibrosis of the liver, and acute and chronic allograft rejection after organ transplantation, and diseases that have an inflammatory component.

49. Method according to claim 39, where said proliferate skin disorder is selected from the group comprising psoriasis, atopic dermatitis, non-specific dermatitis primary irritant contact-dermatitis, allergic contact-dermatitis, lamellar ichthyosis, epidermolytic hyperkeratoses, pre-malign sun-induced keratoses, and seborrhoea.

50. Method according to claim 1, wherein said composition is administered or fed to an animal.

51. Method according to claim 39, wherein said composition is administered or fed to an animal.

52. Method according to claim 5, wherein said animal is a human.

53. Method according to claim 50, wherein said animal is a human.

54. Method according to claim 51, wherein said animal is a human.

55. Method according to claim 5, wherein said animal is an agricultural animal.

56. Method according to claim 50, wherein said animal is an agricultural animal.

57. Method according to claim 51, wherein said animal is an agricultural animal.

58. Method according to claim 5, wherein said animal is a domestic or pet animal.

59. Method according to claim 50, wherein said animal is a domestic or pet animal.

60. Method according to claim 51, wherein said animal is a domestic or pet animal.

61. Method according to claim 5, wherein said animal is a fish or shellfish.

62. Method according to claim 50, wherein said animal is a fish or shellfish.

63. Method according to claim 51, wherein said animal is a fish or shellfish.

64. Method according to claim 1, where the compounds comprising non β-oxidizable fatty acid entities comprise a daily dosage of about 1-200 mg/kg for human consumption, and about 1-2000 mg/kg for animal consumption.

65. Method according to claim 5, where the compounds comprising non β-oxidizable fatty acid entities comprise a daily dosage of about 1-200 mg/kg for human consumption, and about 1-2000 mg/kg for animal consumption.

66. Method according to claim 1, where the protein material comprise a daily dosage of about 5-500 mg/kg for human consumption, and from 5 mg/kg up to the total daily protein consumption for animal consumption.

67. Method according to claim 5, where the protein material comprise a daily dosage of about 5-500 mg/kg for human consumption, and from 5 mg/kg up to the total daily protein consumption for animal consumption.

68. Method according to claim 39, where the protein material comprise a daily dosage of about 5-500 mg/kg for human consumption, and from 5 mg/kg up to the total daily protein consumption for animal consumption.

69. Method according to claim 37, where the oil comprise a daily dosage of about 1-300 mg/kg for human consumption, and from 1 mg/kg up to the total daily fat consumption for animal consumption.

70. Method according to claim 38, where the oil comprise a daily dosage of about 1-300 mg/kg for human consumption, and from 1 mg/kg up to the total daily fat consumption for animal consumption.

71. Method according to claim 39, where the oil comprise a daily dosage of about 1-300 mg/kg for human consumption, and from 1 mg/kg up to the total daily fat consumption for animal consumption.

72. Method according to claim 5, where the animal feed is at least one selected from the group comprising a nutritional composition, veterinary composition, and a functional food product.

73. A composition, comprising a combination of:
   1) a protein material; and
   2) one or more compounds comprising non β-oxidizable fatty acid entities represented by
      (a) the general formula R"—COO—(CH$_2$)$_{2n+1}$—X—R', wherein X is a sulphur atom, a selenium atom, an oxygen atom, a CH$_2$ group, a SO group or a SO$_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a CH$_2$ group, a SO group and a SO$_2$ group; and R" is a hydrogen atom or an alkyl group containing from 1 to 4 carbon atoms; and/or (b) the general formula (I),

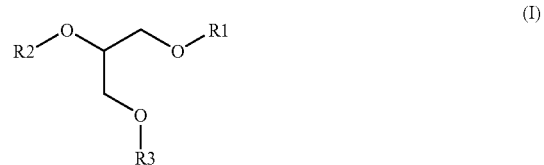

wherein R1, R2, and R3 represent
   i) a hydrogen atom; or
   ii) a group having the formula CO—R in which R is a linear or branched alkyl group, saturated or unsaturated, optionally substituted, and the main chain of said R contains from 1 to 25 carbon atoms; or
   iii) a group having the formula CO—(CH$_2$)$_{2n+1}$—X—R', wherein X is a sulphur atom, a selenium atom, an oxygen atom, a CH$_2$ group, a SO group or a SO$_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a CH$_2$ group, a SO group and a SO$_2$ group;
   iv) an entity selected from the group comprising —PO$_3$CH$_2$CHNH$_3$COOH (serine), PO$_3$CH$_2$CH$_2$NH$_3$ (ethanolamine), PO$_3$CH$_2$CH$_2$N(CH$_3$)$_3$ (choline), PO$_3$CH$_2$CHOHCH$_2$OH (glycerol) and PO$_3$(CHOH)$_6$ (inositol);

wherein R1, R2, and R3 are chosen independently from i), ii), iii), or iv), but at least one of R1, R2, or R3 is defined by iii); and/or (c) the general formula (II),

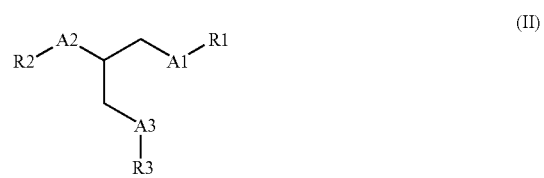

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;

wherein R1, R2, and R3 represent;
   i) a hydrogen atom or a linear or branched alkyl group, saturated or unsaturated, optionally substituted, containing from 1 to 23 carbon atoms; or
   ii) a group having the formula CO—R in which R is a linear or branched alkyl group, saturated or unsaturated, optionally substituted, and the main chain of said R contains from 1 to 25 carbon atoms; or iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;

iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);

wherein R1, R2, and R3 are chosen independently from i), ii), iii), or iv), but at least one of R1, R2, or R3 is defined by iii); and/or a salt, prodrug or complex of the compounds according to (a)-(c).

74. Composition according to claim 73, wherein said protein material is fermented.

75. Composition according to claim 73, wherein said protein material is a single cell protein material (SCP).

76. Composition according to claim 73, wherein said protein material is a fish protein hydrolysate.

77. Composition according to claim 73, where said protein material is soy protein.

78. Composition according to claim 77, wherein said protein material is a fermented soy protein material.

79. Composition according to claim 78, wherein said soy protein material is GENDAXIN® (isoflavone concentrate).

80. Composition according to claim 73, where the composition comprise a daily dosage of a compound comprising a non β-oxidizable fatty acid analogue of about 1-200 mg/kg for human consumption, and about 1-2000 mg/kg for animal consumption.

81. Composition according to claim 73, wherein the composition further comprises a plant and/or fish oil.

82. Composition according to claim 73, where the compound(s) comprising a non β-oxidizable fatty acid entity are non β-oxidizable fatty acids.

83. Composition according to claim 82, where the compound(s) comprising a non β-oxidizable fatty acid entity are tetradecylthioacetic acid (TTA), tetradecylselenoacetic acid and/or 3-Thia-15-heptadecyne.

84. Composition according to claim 73, where X is a sulphur atom or a selenium atom.

85. Composition according to claim 73, where the compound(s) comprising a non β-oxidizable fatty acid entity is a phospholipid, wherein said phospholipid is selected from the group comprising phosphatidyl serine, phosphatidyl choline, phosphatidyl ethanolamine, phosphatidyl inositol, phosphatidyl glycerol, and/or diphosphatidyl glycerol.

86. Composition according to claim 73, where the compound comprising a non β-oxidizable fatty acid entity is the phosphatidyl choline derivative 1,2-ditetradecylthioacetoyl-sn-glycero-3-phosphocholine.

87. Composition according to claim 73, where the compound comprising a non β-oxidizable fatty acid entity is the phosphatidyl ethanolamine derivative 1,2-ditetradecylthioacetoyl-sn-glycero-3-phosphoethanolamine.

88. Composition according to claim 73, where the compound(s) comprising a non β-oxidizable fatty acid entity are mono-, di- or tri-acylglycerides.

89. Composition according to claim 88, where the compound(s) comprising a non β-oxidizable fatty acid entity are tri-acylglycerides comprising tetradecylthioacetic acid (TTA).

90. A composition comprising a combination of:
1) a protein material, and;
2) a plant or fish oil,
wherein the protein material is chosen from the group comprising single cell protein material (SCP), fish protein hydrolysate, or a fermented soy protein material.

91. Method according to claim 90, wherein said protein material is GENDAXIN® (isoflavone concentrate).

92. Composition according to claim 73, where the plant or fish oil comprise polyunsaturated fatty acids.

93. Composition according to claim 90, where the plant or fish oil comprise polyunsaturated fatty acids.

94. Composition according to claim 90, where the plant oil is selected from the group comprising sunflower oil, soy oil and olive oil.

95. Composition according to claim 73, where the composition comprises a daily dosage of protein material of about 5-500 mg/kg for human consumption, and from 5 mg/kg up to the total daily protein consumption for animal consumption.

96. Composition according to claim 90, where the composition comprises a daily dosage of protein material of about 5-500 mg/kg for human consumption, and from 5 mg/kg up to the total daily protein consumption for animal consumption.

97. Composition according to claim 73, where the composition comprises a daily dosage of oil of about 1-300 mg/kg for human consumption, and from 1 mg/kg up to the total daily fat consumption for animal consumption.

98. Composition according to claim 90, where the composition comprises a daily dosage of oil of about 1-300 mg/kg for human consumption, and from 1 mg/kg up to the total daily fat consumption for animal consumption.

99. Composition according to claim 73, wherein the composition is an animal feed further comprising common feed components.

100. Composition according to claim 90, wherein the composition is an animal feed further comprising common feed components.

101. Composition according to claim 73, wherein the animal feed is a fish feed.

102. Composition according to claim 90, wherein the animal feed is a fish feed.

103. Composition according to claim 73, where the fish feed is salmon feed.

104. Composition according to claim 90, where the fish feed is salmon feed.

105. Composition according to claim 73, where the common feed components comprise fishmeal and/or fish oil.

106. Composition according to claim 90, where the common feed components comprise fishmeal and/or fish oil.

107. Method for producing an animal based product with improved fatty acid composition, comprising of feeding the animal from which the product is to be produced with an animal feed comprising common feed components and a combination of:
1) a protein material; and
2) one or more compounds comprising non β-oxidizable fatty acid entities represented by
(a) the general formula R"—COO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group; and R" is a hydrogen atom or an alkyl group containing from 1 to 4 carbon atoms; and/or (b) the general formula (I),

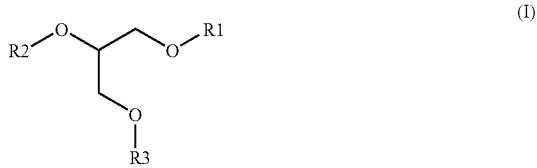

wherein R1, R2, and R3 represent
i) a hydrogen atom; or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or (c) the general formula (II),

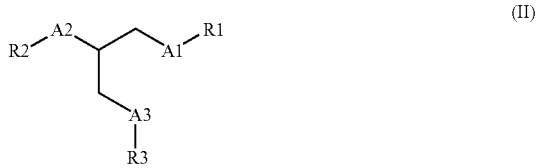

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;
wherein R1, R2, and R3 represent
i) a hydrogen atom or a linear or branched alkyl group, saturated or unsaturated, optionally substituted, containing from 1 to 23 carbon atoms or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or
a salt, prodrug or complex of the compounds according to (a)-(c).

108. Method for producing an animal based product with improved fatty acid composition, comprising of feeding the animal from which the product is to be produced with an animal feed comprising common feed components and a protein material and optionally a non β-oxidizable fatty acid analogue.

109. Method according to claim 107, wherein the animal feed further comprises fermented soy protein material.

110. Method according to claim 108, wherein the animal feed further comprises fermented soy protein material.

111. Method according to claim 107, where the animal based product is a meat product.

112. Method according to claim 108, where the animal based product is a meat product.

113. Method according to claim 107, where the animal based product is an oil based product.

114. Method according to claim 108, where the animal based product is an oil based product.

115. Method according to claim 107, where the animal based product is a skin based product.

116. Method according to claim 108, where the animal based product is a skin based product.

117. A method of prevention of insulin resistance, obesity, diabetes, fatty liver, hypercholesterolemia, dyslipidemia, atherosclerosis, coronary heart disease, thrombosis, stenosis, secondary stenosis, myocardial infarction, stroke, elevated blood pressure, endothelial dysfunction, procoagulant state, polycystic ovary syndrome, the metabolic syndrome, reducing the growth of cancer cells and/or inhibiting the metastasis of metastatic neoplasms, an inflammatory disorder, and a proliferate skin disorder comprising the administration of a pharmaceutical or nutritional composition comprising a combination of:
1) a protein material; and
2) one or more compounds comprising non β-oxidizable fatty acid entities represented by
(a) the general formula R"—COO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group; and R" is a hydrogen atom or an alkyl group containing from 1 to 4 carbon atoms; and/or (b) the general formula (I),

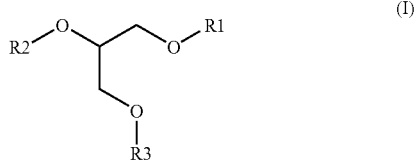

wherein R1, R2, and R3 represent
i) a hydrogen atom; or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or (c) the general formula (II),

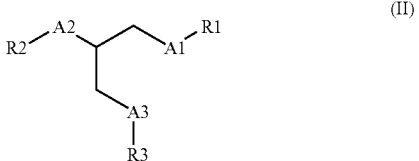

wherein A1, A2 and A3 are chosen independently and represent an oxygen atom, a sulphur atom or an N—R4 group in which R4 is a hydrogen atom or a linear or branched alkyl group, saturated or unsaturated, optionally substituted, containing from 1 to 5 carbon atoms;
wherein R1, R2, and R3 represent
i) a hydrogen atom or a linear or branched alkyl group, saturated or unsaturated, optionally substituted, containing from 1 to 23 carbon atoms or
ii) a group having the formula CO—R in which R is a linear or branched alkyl group, saturated or unsaturated, optionally substituted, and the main chain of said R contains from 1 to 25 carbon atoms; or
iii) a group having the formula CO—$(CH_2)_{2n+1}$—X—R', wherein X is a sulphur atom, a selenium atom, an oxygen atom, a $CH_2$ group, a SO group or a $SO_2$ group; n is an integer of 0 to 11; and R' is a linear or branched alkyl group, saturated or unsaturated, optionally substituted, wherein the main chain of said R' contains from 13 to 23 carbon atoms and optionally one or more heterogroups selected from the group comprising an oxygen atom, a sulphur atom, a selenium atom, an oxygen atom, a $CH_2$ group, a SO group and a $SO_2$ group;
iv) an entity selected from the group comprising —$PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol) and $PO_3(CHOH)_6$ (inositol);
wherein R1, R2, and R3 are chosen independently from i), ii), iii), or iv), but at least one of R1, R2, or R3 is defined by iii); and/or
a salt, prodrug or complex of the compounds according to (a)-(c).

118. Method according to claim 117, where said prevention of the growth of cancer cells and/or inhibiting the metastasis of metastatic neoplasms includes inhibition of: primary and secondary neoplasms, the growth of tumours, invasion of a primary tumour into connective tissue and formation of secondary tumours.

119. Method according to claim 117, where the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders, various immune mediated neurological disorders, various cardiovascular disorders, inflammatory bowel diseases and Chron's disease, non specific colitis, pancreatitis, nephritis, cholestatis/fibrosis of the liver, and acute and chronic allograft rejection after organ transplantation, and diseases that have an inflammatory component.

120. Method according to claim 117, where said proliferate skin disorder is selected from the group comprising psoriasis, atopic dermatitis, non-specific dermatitis, primary irritant contact-dermatitis, allergic contact-dermatitis, lamellar ichthyosis, epidermolytic hyperkeratoses, pre-malign sun-induced keratoses, and seborrhoea.

121. Method according to claim 117, wherein said protein material is fermented.

122. Method according to claim 117, wherein said protein material is a single cell protein material (SCP).

123. Method according to claim 117, where said protein material is soy protein.

124. Method according to claim 117, wherein said protein material is GENDAXIN® (isoflavone concentrate).

125. Method according to claim 117, where the compound(s) comprising a non β-oxidizable fatty acid entity are non β-oxidizable fatty acids.

126. Method according to claim 117, where the compound(s) comprising a non β-oxidizable fatty acid entity are tetradecylthioacetic acid (TTA), tetradecylselenoacetic acid and/or 3-Thia-15-heptadecyne.

127. Method according to claim 117, where X is a sulphur atom or a selenium atom.

128. Method according to claim 117, where the compound(s) comprising a non β-oxidizable fatty acid entity is a phospholipid, wherein said phospholipid is selected from the group comprising phosphatidyl serine, phosphatidyl choline, phosphatidyl ethanolamine, phosphatidyl inositol, phosphatidyl glycerol, and/or diphosphatidyl glycerol.

129. Method according to claim 117, where the compound comprising a non β-oxidizable fatty acid entity is the phosphatidyl choline derivative 1,2-ditetradecylthioacetoyl-sn-glycero-3-phosphocholine.

130. Method according to claim 117, where the compound comprising a non β-oxidizable fatty acid entity is the phosphatidyl ethanolamine derivative 1,2-ditetradecylthioacetoyl-3-phosphoethanolamine.

131. Method according to claim 117, where the compound(s) comprising a non β-oxidizable fatty acid entity are tri-acylglycerides comprising tetradecylthioacetic acid (TTA).

132. Method according to claim 117, wherein the composition or animal feed further comprises a plant and/or fish oil.

133. A method of prevention of hypercholesterolemia and conditions negatively effected by high cholesterol levels, insulin resistance, obesity, diabetes, fatty liver, dyslipidemia, atherosclerosis, coronary heart disease, thrombosis, stenosis, secondary stenosis, myocardial infarction, stroke, elevated blood pressure, endothelial dysfunction, procoagulant state, polycystic ovary syndrome, the metabolic syndrome, reducing the growth of cancer cells and/or inhibiting the metastasis of metastatic neoplasms, inflammatory disorders and proliferate skin disorders comprising the administration of a preparation comprising a combination of:
1) a protein material, and
2) a plant or fish oil,
wherein the protein material is chosen from the group comprising single cell protein material (SCP), fish protein hydrolysate, and a fermented soy protein material.

134. Method according to claim 133, wherein said protein material is GENDAXIN® (isoflavone concentrate).

135. Method according to claim 132, where the plant or fish oil comprise polyunsaturated fatty acids.

136. Method according to claim 133, where the plant or fish oil comprise polyunsaturated fatty acids.

137. Method according to claim 132, where the plant oil is selected from the group comprising sunflower oil, soy oil and olive oil.

138. Method according to claim 133, where the plant oil is selected from the group comprising sunflower oil, soy oil and olive oil.

139. Method according to claim 133, where said prevention of the growth of cancer cells and/or inhibiting the metastasis of metastatic neoplasms includes inhibition of: primary and secondary neoplasms, the growth of tumours, invasion of a primary tumour into connective tissue and formation of secondary tumours.

140. Method according to claim 133, where the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders, various immune mediated neurological disorders, various cardiovascular disorders, inflammatory bowel diseases and Chron's disease, non specific colitis, pancreatitis, nephritis, cholestatis/fibrosis of the liver, and acute and chronic allograft rejection after organ transplantation, and diseases that have an inflammatory component.

141. Method according to claim 133, where said proliferate skin disorder is selected from the group comprising psoriasis, atopic dermatitis, non-specific dermatitis, primary irritant contact-dermatitis, allergic contact-dermatitis, lamellar ichthyosis, epidermolytic hyperkeratoses, pre-malign sun-induced keratoses, and seborrhoea.

142. Method according to claim 117, wherein said composition is administered or fed to an animal.

143. Method according to claim 133, wherein said composition is administered or fed to an animal.

144. Method according to claim 142, wherein said animal is a human.

145. Method according to claim 143, wherein said animal is a human.

146. Method according to claim 142, wherein said animal is an agricultural animal.

147. Method according to claim 143, wherein said animal is an agricultural animal.

148. Method according to claim 143, wherein said animal is a domestic or pet animal.

149. Method according to claim 142, wherein said animal is a fish or shellfish.

150. Method according to claim 143, wherein said animal is a fish or shellfish.

151. Method according to claim 117, where the compounds comprising non β-oxidizable fatty acid entities comprise a daily dosage of about 1-200 mg/kg for human consumption, and about 1-2000 mg/kg for animal consumption.

152. Method according to claim 117, where the protein material comprise a daily dosage of about 5-500 mg/kg for human consumption, and from 5 mg/kg up to the total daily protein consumption for animal consumption.

153. Method according to claim 133, where the protein material comprise a daily dosage of about 5-500 mg/kg for human consumption, and from 5 mg/kg up to the total daily protein consumption for animal consumption.

154. Method according to claim 132, where the oil comprise a daily dosage of about 1-300 mg/kg for human consumption, and from 1 mg/kg up to the total daily fat consumption for animal consumption.

155. Method according to claim 133, where the oil comprise a daily dosage of about 1-300 mg/kg for human consumption, and from 1 mg/kg up to the total daily fat consumption for animal consumption.

* * * * *